US009693796B2

(12) United States Patent
Rydberg

(10) Patent No.: US 9,693,796 B2
(45) Date of Patent: Jul. 4, 2017

(54) ROTATIONAL ATHERECTOMY DEVICE WITH EXCHANGEABLE DRIVE SHAFT AND MESHING GEARS

(71) Applicant: Cardiovascular Systems, Inc., St. Paul, MN (US)

(72) Inventor: Nicholas W. Rydberg, Oakdale, MN (US)

(*) Notice: Subject to any disclaimer, the term of this patent is extended or adjusted under 35 U.S.C. 154(b) by 282 days.

(21) Appl. No.: 14/492,910

(22) Filed: Sep. 22, 2014

(65) Prior Publication Data

US 2015/0119909 A1 Apr. 30, 2015

Related U.S. Application Data

(62) Division of application No. 14/340,353, filed on Jul. 24, 2014, now Pat. No. 9,439,674.

(60) Provisional application No. 61/950,402, filed on Mar. 10, 2014, provisional application No. 61/858,345, filed on Jul. 25, 2013.

(51) Int. Cl.
*A61B 17/3207* (2006.01)
*A61B 90/98* (2016.01)
*A61B 17/00* (2006.01)

(52) U.S. Cl.
CPC ...... *A61B 17/320758* (2013.01); *A61B 90/98* (2016.02); *A61B 2017/0046* (2013.01); *A61B 2017/00398* (2013.01); *A61B 2017/00473* (2013.01); *A61B 2017/00477* (2013.01); *A61B 2017/00526* (2013.01); *A61B 2017/00991* (2013.01); *Y10T 29/4984* (2015.01)

(58) Field of Classification Search
CPC ........ A61B 17/320758; A61B 17/1617; A61B 17/1622; A61B 17/1628; A61B 2017/000398; A61B 2017/00464; A61B 2017/00469; A61B 2017/00473; A45D 29/14; B25F 5/001; B25F 5/02; B25F 3/00; B25F 1/02; B25F 1/04
USPC .......................... 606/159, 180; 408/141, 142
See application file for complete search history.

(56) References Cited

U.S. PATENT DOCUMENTS 2,261,230 A * 11/1941 Cox ...................... A61B 17/14
30/500
3,357,275 A * 12/1967 Green, Jr. ............. B23B 45/001
74/606 R (Continued)

FOREIGN PATENT DOCUMENTS

DE 10300127 A1 7/2004

OTHER PUBLICATIONS

International Search Report and Written Opinion, mailed Dec. 3, 2015 for International Application No. PCT/US2015/47881, filed Sep. 1, 2015.

(Continued)

*Primary Examiner* — Kathleen Holwerda
(74) *Attorney, Agent, or Firm* — Barnes & Thornburg, LLP

(57) ABSTRACT

An atherectomy device with an exchangeable drive shaft is disclosed, having a drive shaft gear at a distal end of the exchangeable drive shaft for meshing engagement with a prime mover gear on the output shaft of the prime mover. The exchangeable drive shaft is inserted into an opening at the distal end of the handle housing and moved axially in a proximal direction. Surface features on at least the prime mover housing and the engageable drive shaft help to align the drive shaft gear with the prime mover gear for meshing engagement.

15 Claims, 14 Drawing Sheets

(56) References Cited

U.S. PATENT DOCUMENTS

| | | | |
|---|---|---|---|
| 4,050,528 A | 9/1977 | Foltz et al. | |
| 4,181,998 A | 1/1980 | Nelson | |
| 4,269,075 A * | 5/1981 | Crist | B23Q 1/0063 285/305 |
| 4,963,147 A | 10/1990 | Agee et al. | |
| 5,480,409 A | 1/1996 | Riza | |
| 5,632,754 A | 5/1997 | Farley et al. | |
| 5,634,933 A | 6/1997 | McCombs et al. | |
| 5,643,297 A | 7/1997 | Nordgren et al. | |
| 5,643,298 A | 7/1997 | Nordgren et al. | |
| 5,653,713 A | 8/1997 | Michelson | |
| 5,700,265 A | 12/1997 | Romano | |
| 5,746,758 A | 5/1998 | Nordgren et al. | |
| 5,766,190 A | 6/1998 | Wulfman | |
| 5,779,130 A | 7/1998 | Alesi et al. | |
| 5,779,722 A | 7/1998 | Shturman et al. | |
| 5,849,023 A | 12/1998 | Mericle | |
| 5,868,767 A | 2/1999 | Farley et al. | |
| 5,888,200 A | 3/1999 | Walen | |
| 5,928,241 A | 7/1999 | Menut et al. | |
| 5,938,670 A | 8/1999 | Keith et al. | |
| 6,024,749 A | 2/2000 | Shturman et al. | |
| 6,042,593 A | 3/2000 | Storz et al. | |
| 6,077,282 A * | 6/2000 | Shturman | A61B 17/320758 606/159 |
| 6,080,171 A | 6/2000 | Keith et al. | |
| 6,129,734 A | 10/2000 | Shturman et al. | |
| 6,280,332 B1 | 8/2001 | Knutson | |
| 6,398,755 B1 | 6/2002 | Belef et al. | |
| 6,436,111 B1 | 8/2002 | Kadavy et al. | |
| 6,537,279 B1 | 3/2003 | Michelson | |
| 6,818,001 B2 | 11/2004 | Wulfman et al. | |
| 6,818,005 B2 | 11/2004 | Kupferschmid et al. | |
| 6,824,550 B1 | 11/2004 | Noriega et al. | |
| 6,958,071 B2 | 10/2005 | Carusillo et al. | |
| 7,118,564 B2 | 10/2006 | Richie et al. | |
| 7,237,990 B2 | 7/2007 | Deng | |
| 7,485,127 B2 | 2/2009 | Nistal | |
| 7,628,763 B2 | 12/2009 | Noriega et al. | |
| 7,674,272 B2 | 3/2010 | Torrance et al. | |
| 8,043,314 B2 | 10/2011 | Noriega et al. | |
| 8,137,370 B2 | 3/2012 | Deng | |
| 8,353,897 B2 | 1/2013 | Doyle et al. | |
| 8,353,922 B2 | 1/2013 | Noriega et al. | |
| 8,388,636 B2 | 3/2013 | Shturman et al. | |
| 8,398,634 B2 | 3/2013 | Manzo et al. | |
| 9,439,674 B2 * | 9/2016 | Rydberg | A61B 17/320758 |
| 2002/0077638 A1 | 6/2002 | Kadavy et al. | |
| 2003/0078594 A1 | 4/2003 | Shturman et al. | |
| 2006/0020282 A1 | 1/2006 | Henniges et al. | |
| 2006/0079889 A1 | 4/2006 | Scott | |
| 2006/0253127 A1 | 11/2006 | Bjerken | |
| 2008/0004644 A1 | 1/2008 | To et al. | |
| 2008/0004645 A1 | 1/2008 | To et al. | |
| 2008/0004646 A1 | 1/2008 | To et al. | |
| 2008/0004647 A1 | 1/2008 | To et al. | |
| 2008/0029574 A1 | 2/2008 | Shelton et al. | |
| 2008/0033423 A1 | 2/2008 | Peacock | |
| 2008/0045986 A1 | 2/2008 | To et al. | |
| 2008/0185419 A1 | 8/2008 | Smith et al. | |
| 2009/0270812 A1 | 10/2009 | Litscher et al. | |
| 2009/0292304 A1 | 11/2009 | Malackowski | |
| 2010/0125276 A1 | 5/2010 | Palermo | |
| 2010/0125287 A1 | 5/2010 | Cole et al. | |
| 2010/0168834 A1 | 7/2010 | Ryan et al. | |
| 2010/0318101 A1 * | 12/2010 | Choi | A61B 34/30 606/130 |
| 2011/0087254 A1 | 4/2011 | Welty | |
| 2011/0124961 A1 | 5/2011 | Zimmon | |
| 2011/0196286 A1 | 8/2011 | Robertson et al. | |
| 2011/0213391 A1 * | 9/2011 | Rivers | A61B 17/320758 606/159 |
| 2011/0282374 A1 * | 11/2011 | Ambardekar | A61B 17/32002 606/176 |
| 2012/0046679 A1 | 2/2012 | Patel et al. | |
| 2012/0083815 A1 | 4/2012 | Troendle | |
| 2012/0109007 A1 | 5/2012 | Rhad | |
| 2012/0116388 A1 | 5/2012 | Houser et al. | |
| 2013/0165908 A1 | 6/2013 | Purdy et al. | |
| 2014/0000411 A1 | 1/2014 | Shelton, IV et al. | |

OTHER PUBLICATIONS

International Search Report and Written Opinion, mailed Nov. 26, 2014, for PCT Application No. PCT/US2014/048173, filed Jul. 25, 2014.

International Search Report and Written Opinion, mailed Jan. 28, 2016, for PCT Application No. PCT/US2015/059231, filed Nov. 5, 2015.

International Search Report and Written Opinion, mailed Dec. 30, 2015, for PCT Application No. PCT/US2015/054143, filed Oct. 6, 2015.

International Search Report and Written Opinion, mailed Dec. 28, 2015, for PCT Application No. PCT/US2015/054026, filed Oct. 5, 2015.

* cited by examiner

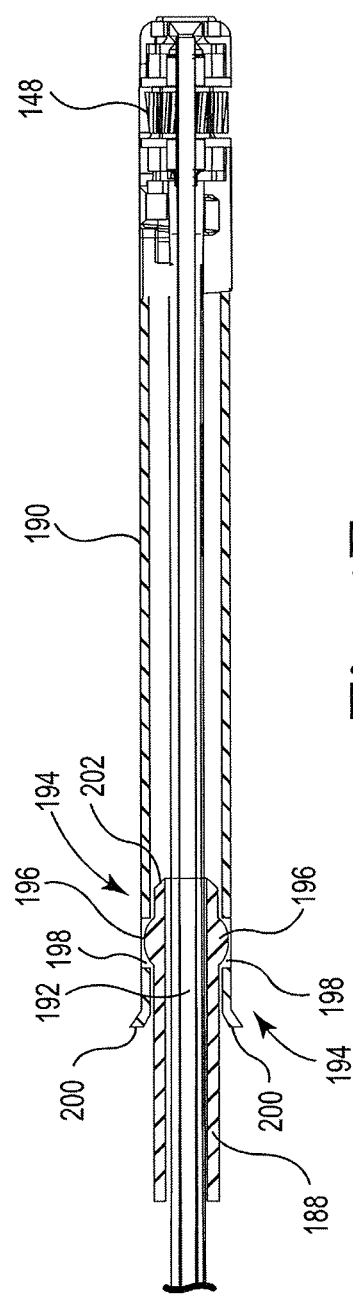
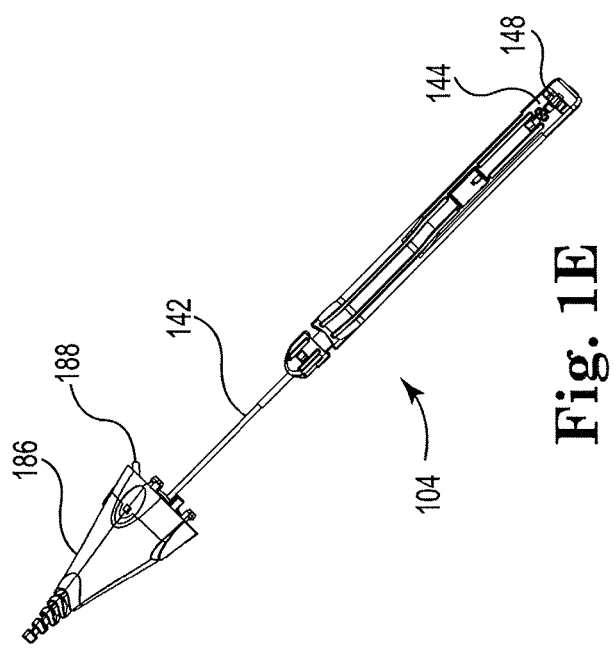
Fig. 1F
Fig. 1E

ROTATIONAL ATHERECTOMY DEVICE WITH EXCHANGEABLE DRIVE SHAFT AND MESHING GEARS

CROSS-REFERENCE TO RELATED APPLICATIONS

This application is a divisional of U.S. patent application Ser. No. 14/340,353 filed Jul. 24, 2014 which claims the benefit of U.S. Provisional Application No. 61/950,402, filed Mar. 10, 2014, and the benefit of U.S. Provisional Application No. 61/858,345 filed Jul. 25, 2013, the entirety of which prior filed applications are hereby incorporated by reference.

STATEMENT REGARDING FEDERALLY SPONSORED RESEARCH OR DEVELOPMENT

Not Applicable

BACKGROUND OF THE INVENTION

Field of the Invention

The disclosure relates to devices and methods for removing tissue from body passageways, such as removal of atherosclerotic plaque from arteries, utilizing a rotational atherectomy device. In particular, the disclosure relates to improvements in a rotational atherectomy device having an exchangeable drive shaft.

Description of the Related Art

A variety of techniques and instruments have been developed for use in the removal or repair of tissue in arteries and similar body passageways. A frequent objective of such techniques and instruments is the removal of atherosclerotic plaque in a patient's arteries. Atherosclerosis is characterized by the buildup of fatty deposits (atheromas) in the intimal layer (i.e., under the endothelium) of a patient's blood vessels. Very often over time what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

Several kinds of atherectomy devices have been developed for attempting to remove some or all of such stenotic material. In one type of device, such as that shown in U.S. Pat. No. 4,990,134 (Auth), a rotating burr covered with an abrasive cutting material, such as diamond grit (diamond particles or dust), is carried at the distal end of a flexible, rotatable drive shaft.

U.S. Pat. No. 5,314,438 (Shturman) shows another atherectomy device having a rotatable drive shaft with a section of the drive shaft having an enlarged diameter, at least a segment of this enlarged diameter section being covered with an abrasive material to define an abrasive segment of the drive shaft. When rotated at high speeds, the abrasive segment is capable of removing stenotic tissue from an artery.

U.S. Pat. No. 5,314,407 (Auth) shows details of a type of handle which may be used in conjunction with rotational atherectomy devices of the type shown in the Auth '134 and Shturman '438 patents. A handle of the type shown in the Auth '407 patent has been commercialized by Heart Technology, Inc. (Redmond, Wash.), now owned by Boston Scientific Corporation (Natick, Mass.) in the rotational atherectomy device sold under the trademark Rotablator®.

The handle of the Rotablator® device includes a variety of components, including a compressed gas driven turbine, a mechanism for clamping a guide wire extending through the drive shaft, portions of a fiber optic tachometer, and a pump for pumping saline through the drive shaft.

The connection between the drive shaft (with its associated burr) and the turbine in the Rotablator® device is permanent; yet, frequently it is necessary to use more than one size burr during an atherectomy procedure. That is, often a smaller size burr is first used to open a stenosis to a certain diameter, and then one or more larger size burrs are used to open the stenosis further. Such use of multiple burrs of subsequently larger diameter is sometimes referred to as a "step up technique" and is recommended by the manufacturer of the Rotablator® device. In the multiple burr technique it is necessary to use a new Rotablator® device for each such successive size burr. Accordingly, there is a need for an atherectomy system that would permit a physician to use only one handle throughout an entire procedure and to attach to such handle an appropriate drive shaft and tissue removing implement (e.g., a burr) to initiate the procedure and then exchange the drive shaft and the tissue removing implement for a drive shaft having a tissue removing implement of a different size or even a different design.

A subsequent version of the Rotablator® has been introduced with the ability to exchange a flexible distal portion of the drive shaft together with a burr for another distal portion of a drive shaft having a different size burr. Technical details of such a system are contained in U.S. Pat. No. 5,766,190, titled "Connectable driveshaft system", and issued on Jun. 16, 1998 to Wulfman. This system utilizes a flexible drive shaft having a connect/disconnect feature allowing the physician to disconnect the exchangeable distal portion of the flexible drive shaft together with the burr from the flexible proximal portion of the drive shaft which is connected to the turbine of the handle, thus permitting the burr size to be changed without discarding the entire atherectomy unit. Each exchangeable drive shaft portion is disposed within its own exchangeable catheter and catheter housing. The flexible proximal portion of the drive shaft in this system is permanently attached to the turbine and is not exchanged. This system has been commercialized by Boston Scientific under the trademark Rotalink System®. While the Rotalink System® does permit one to change the burr size, the steps required to actually disconnect the exchangeable portion of the drive shaft and replace it with another exchangeable portion of the drive shaft are quite involved and require relatively intricate manipulation of very small components.

First, a catheter housing must be disconnected from the handle and moved distally away from the handle to expose portions of both the proximal and distal sections of the flexible drive shaft which contain a disconnectable coupling. This coupling is disconnected by sliding a lock tube distally, permitting complementary lock teeth on the proximal and distal portions of the flexible drive shaft to be disengaged from each other. A similar flexible distal drive shaft portion with a different burr may then be connected to the flexible proximal portion of the drive shaft. To accomplish such assembly, the lock tooth on the proximal end of the distal replacement portion of the drive shaft must first be both longitudinally and rotationally aligned with the complementary lock tooth at the distal end of the proximal portion of the drive shaft. Since the flexible drive shaft typically is less than 1 mm in diameter, the lock teeth are similarly quite small in size, requiring not insignificant manual dexterity and visual acuity to properly align and interlock the lock teeth. Once the lock teeth have been properly interlocked with each other, the lock tube (also having a very small diameter) is slid proximally to secure the coupling. The catheter housing must then be connected to the handle housing.

While this system does permit one to exchange one size burr (together with a portion of the drive shaft) for a burr of another size, the exchange procedure is not an easy one and must be performed with considerable care. The individual performing the exchange procedure must do so while wearing surgical gloves to protect the individual from the blood of the patient and to maintain the sterility of the elements of the system. Surgical gloves diminish the tactile sensations of the individual performing the exchange procedure and therefore make such exchange procedure even more difficult.

In recent years, there has been an effort to develop an atherectomy device with easier attachment and/or exchange of the drive shaft and its tissue removing implement.

For instance, U.S. Pat. No. 6,024,749 (Shturman et al), U.S. Pat. No. 6,077,282 (Shturman et al), U.S. Pat. No. 6,129,734 (Shturman et al) and U.S. Pat. No. 6,852,118 (Shturman et al), all incorporated by reference in their entirety herein, disclose an atherectomy device having an exchangeable drive shaft cartridge comprising a housing that is removably attachable to the device's handle housing. The exchangeable cartridge includes a longitudinally movable tube that is removably attached to the prime mover carriage and a rotatable drive shaft that is removably attachable to the prime mover. A coupling is provided which connects the longitudinally extendible tube to the prime mover while indexing the relative position of the longitudinally extendible tube and the proximal portion of the drive shaft. U.S. Patent Publication No. 2011/0087254 (Welty), incorporated by reference in its entirety herein, discloses an atherectomy device where the prime mover has a prime mover coupler and the drive shaft has a drive shaft coupler that is engageable with the prime mover coupler. The drive shaft coupler and prime mover coupler have engageable lateral cross-sections that are complementary and geometrically keyed to one another. When they are engaged to one another, the complementary cross-sections allow axial translation between the drive shaft coupler and the prime mover coupler while prohibiting rotational coupler between the drive shaft coupler and the prime mover coupler.

Other atherectomy devices, such as U.S. Patent Pub. No. 2011/0077673 (Grubac et al), utilize a magnetic clutch connection between the drive shaft and the prime mover. The drive shaft and the prime mover are held together longitudinally by a magnetic attractive force between the motor plate and the drive shaft plate. The torques between the motor and the drive shaft are transmitted completely between the motor plate and the drive shaft plate and, when below a threshold torque, the motor plate and the drive shaft plate remain held together rotationally by static friction. When the torques between the motor and the drive shaft are greater than the threshold torque, the motor plate and the drive shaft plate slip rotationally past each other, causing a residual torque to be transmitted between the motor and the drive shaft.

Although the above devices utilize friction or magnetic couplings to removably engage the drive shaft with the prime mover, some atherectomy devices have a driveshaft driven by a pair of mating gears, one gear connected to the drive shaft and one gear connected to the mating gear. Due to this gearing arrangement, the atherectomy device is generally restricted to one shaft size per assembly. Typically the gear connected to the drive shaft is not replaced, so any exchangeable drive shaft must be sized to properly engage with the drive shaft. Thus, multiple atherectomy devices are needed for each desired drive shaft diameter.

Accordingly, there exists a need for an atherectomy device with the mating gear assembly where the drive shaft is exchangeable for another drive shaft of either the same size or another size.

BRIEF SUMMARY OF THE INVENTION

An embodiment of a rotational atherectomy device includes a handle having a proximal section, a distal section having a channel extending proximally from an opening in a distal end of the handle, and an elongated hollow intermediate section between the proximal and the distal sections. The intermediate section includes an opening between an interior thereof and the channel in the distal section, and a slot. The device further includes a prime mover carriage having a prime mover, and a prime mover gear fixedly attached to a shaft of the prime mover. The prime mover carriage is disposed within the interior of the intermediate section. The device further includes a control knob having at least a portion thereof extending through the slot in the intermediate section and operationally coupled to the prime mover carriage such that a longitudinal displacement of the control knob induces a longitudinal displacement of the prime mover carriage. The control knob is operable to an unlocked state for permitting the longitudinal displacement of the control knob, and to a locked state for inhibiting the longitudinal displacement of the control knob. Some embodiments of the device include an exchangeable drive shaft cartridge having a proximal section and a distal section, and a drive shaft having a proximal end and a distal end. The drive shaft extends through an opening in the distal section of the drive shaft cartridge. The drive shaft cartridge includes a gear engagement assembly having a drive shaft gear fixedly attached to the proximal end of the drive shaft. Some embodiments of the device include one or more connectors for removably connecting the distal section of the handle and the distal section of the drive shaft cartridge to one another. Certain embodiments of the one or more connectors includes complementary first and second sections, wherein the first section of each connector is integrally formed with the distal section of handle, and the complementary second section of each connector is integrally formed with the distal section of the drive shaft cartridge. The device includes at least one alignment element on at least one of the gear engagement assembly, the prime mover carriage and the interior of the intermediate section of the handle. The at least one alignment element is configured for aligning at least the prime mover gear and the drive shaft gear with one another when the gear engagement assembly is extended into the interior of the intermediate section and positioned proximate the prime mover. The device further includes at least one biasing element configured for removably meshing the prime mover gear and the drive shaft gear when the prime mover gear and the drive shaft gear are aligned with one another such that a rotational movement of one of the prime mover and the drive shaft induces a rotational movement in the other.

Another embodiment of a rotational atherectomy device includes a handle having a proximal section, a distal section having a channel extending proximally from an opening in a distal end of the handle, and an elongated intermediate section having a trough extending between the proximal and the distal sections. The device further includes a prime mover carriage having a prime mover, and a prime mover gear fixedly attached to a shaft of the prime mover. The prime mover carriage disposed within the trough of the intermediate section. Some embodiments of the device include an exchangeable drive shaft cartridge having a proximal section and a distal section, a slot in an intermediate section extending between the proximal and the distal sections, a drive shaft having a proximal end and a distal end. The drive shaft extends through an opening in the distal section of the drive shaft cartridge. The drive shaft cartridge includes a gear engagement assembly having a drive shaft gear fixedly attached to the proximal end of the drive shaft, and a control knob having at least a portion thereof extending through the slot and operationally coupled to the drive shaft cartridge such that a longitudinal displacement of the control knob induces a longitudinal displacement of the drive shaft cartridge. The control knob can be operated to an unlocked state for permitting the longitudinal displacement of the control knob, and to a locked state for inhibiting the longitudinal displacement of the control knob. Certain embodiments of the device include one or more connectors for removably connecting the handle and the drive shaft cartridge to one another. Some embodiments of the one or more connectors include complementary first and second sections, wherein the first section is integrally formed with the handle, and the complementary second section is integrally formed with the drive shaft cartridge. The handle and the drive shaft cartridge are removably connected by removably meshing the prime mover gear and the drive shaft gear by juxtaposing the prime mover carriage and the gear engagement assembly, and concurrently displacing the handle and the drive shaft cartridge in opposite directions.

Yet another embodiment of a rotational atherectomy device includes a handle having a proximal section, a distal section having a trough, and an elongated hollow intermediate section between the proximal and the distal sections. The intermediate section includes an opening between an interior thereof and the trough, and a slot. The device further includes a prime mover carriage having a prime mover and a prime mover gear fixedly attached to a shaft of the prime mover. In some embodiments, the prime mover carriage is disposed within the interior of the intermediate section. Some embodiments of the device include a control knob having at least a portion thereof extending through the slot and operationally coupled to the prime mover carriage such that a longitudinal displacement of the control knob induces a longitudinal displacement of the prime mover carriage. The control knob can be operated to an unlocked state for permitting the longitudinal displacement of the control knob, and to a locked state for inhibiting the longitudinal displacement of the control knob. The device further includes an exchangeable drive shaft cartridge having a proximal section and a distal section, and a drive shaft having a proximal end and a distal end. The drive shaft extends through an opening in the distal section of the drive shaft cartridge. The drive shaft cartridge includes a gear engagement assembly having a drive shaft gear fixedly attached to the proximal end of the drive shaft, and one or more connectors for removably connecting the handle and the drive shaft cartridge to one another, wherein each of the one or more connectors includes complementary first and second sections, wherein the first section is integrally formed with the handle and the complementary second section is integrally formed with the drive shaft cartridge. The handle and the drive shaft cartridge are removably connected by inserting at least the gear engagement assembly through the opening in the intermediate section of the handle, removably meshing the prime mover gear and the drive shaft gear by juxtaposing the prime mover carriage and the gear engagement assembly, and displacing the handle and the drive shaft cartridge in opposite directions.

Another embodiment of a rotational atherectomy device includes a handle having a proximal section, a distal section, and an elongated hollow intermediate section between the proximal and the distal sections. The intermediate section includes a door for accessing an interior thereof, an opening between the interior and the distal section, and a slot. The device further includes a prime mover carriage having a prime mover, and a prime mover gear fixedly attached to a shaft of the prime mover. In certain embodiments, the prime mover carriage is disposed within the interior of the intermediate section. Some embodiments of the device include a control knob having at least a portion thereof extending through the slot and operationally coupled to the prime mover carriage such that a longitudinal displacement of the control knob induces a longitudinal displacement of the prime mover carriage. Certain embodiments of the control knob can be operated to an unlocked state for permitting the longitudinal displacement of the control knob, and to a locked state for inhibiting the longitudinal displacement of the control knob. The device further includes an exchangeable drive shaft cartridge having a drive shaft extending between a proximal end and a distal end, and through an opening in a distal section of the drive shaft cartridge. The drive shaft cartridge includes a gear engagement assembly having a drive shaft gear fixedly attached to the proximal end of the drive shaft. Certain embodiments of the device include a first connector for removably and pivotally connecting the prime mover carriage and the gear engagement assembly to one another and for aligning at least the prime mover gear and the drive shaft gear with one another. Some embodiments of the first connector include complementary first and second sections, wherein the first section is integrally formed with the prime mover carriage, and the second section is integrally formed with the gear engagement assembly. The device further includes a second connector for removably connecting the handle and the drive shaft cartridge to one another, wherein removably connecting the handle and the drive shaft cartridge using the second connector removably meshes the prime mover gear and the drive shaft gear, such that a rotational movement of one of the prime mover and the drive shaft induces a rotational movement in the other.

Yet another embodiment of a rotational atherectomy device includes a handle having a proximal section, a distal section having a channel extending proximally from an opening in a distal end of the handle, and an elongated hollow intermediate section between the proximal and the distal sections. The intermediate section includes an opening between an interior thereof and the channel in the distal section, and a slot. Embodiments of the device include a prime mover carriage having a prime mover, and a prime mover gear fixedly attached to a shaft of the prime mover. In certain embodiments, the prime mover carriage is disposed within the interior of the intermediate section. Some embodiments of the device include a control knob having at least a portion thereof extending through the slot and operationally coupled to the prime mover carriage such that a longitudinal displacement of the control knob induces a longitudinal displacement of the prime mover carriage. In certain embodiments, the control knob can be operated to an unlocked state for permitting the longitudinal displacement of the control knob, and to a locked state for inhibiting the longitudinal displacement of the control knob. Embodiments of the device further include an exchangeable drive shaft cartridge having a proximal section and a distal section, a drive shaft extending between a proximal end and a distal end. The drive shaft extends through an opening in the distal section of the drive shaft cartridge. The drive shaft cartridge includes a gear engagement assembly having a drive shaft gear fixedly attached to the proximal end of the drive shaft. Some embodiments of the device include a first connector for removably and pivotally connecting the handle and the drive shaft cartridge to one another, and a second connector for removably connecting the handle and the drive shaft cartridge to one another.

In some embodiments of the device, the first connector is a pivoting connector having complementary first and second sections, wherein the first section is integrally formed with the distal section of the handle, and the complementary second section is integrally formed with the drive shaft cartridge. In certain embodiments, the second connector includes complementary first and second sections, wherein the first section is integrally formed with the handle, and the second section is integrally formed with the proximal section of the drive shaft cartridge. Removably connecting the handle and the drive shaft cartridge using the second connector removably meshes the prime mover gear and the drive shaft gear, such that a rotational movement of one of the prime mover and the drive shaft induces a rotational movement in the other.

In certain embodiments of the device, the first connector is a pivoting connector having complementary first and second sections, wherein the first section is integrally formed with the handle, and the second section is integrally formed with the proximal section of the drive shaft cartridge. In some embodiments, the second connector includes complementary first and second sections, wherein the first section is integrally formed with the distal section of the handle, and the second section is integrally formed with the drive shaft cartridge. At least the prime mover gear and the drive shaft gear are aligned with one another when the handle and the drive shaft cartridge are removably and pivotally connected using the first connector. Removably connecting the handle and the drive shaft cartridge using the second connector removably meshes the prime mover gear and the drive shaft gear, such that a rotational movement of one of the prime mover and the drive shaft induces a rotational movement in the other.

BRIEF DESCRIPTION OF THE SEVERAL VIEWS OF THE DRAWINGS

FIG. 1E is a perspective view of the drive shaft cartridge of FIG. 1D illustrating a drive shaft in a telescoped state;

FIG. 1F is a longitudinal cross-sectional view of at least a portion of a distal section of the drive shaft cartridge of FIG. 1D;

DETAILED DESCRIPTION OF THE INVENTION

Figure 1A:
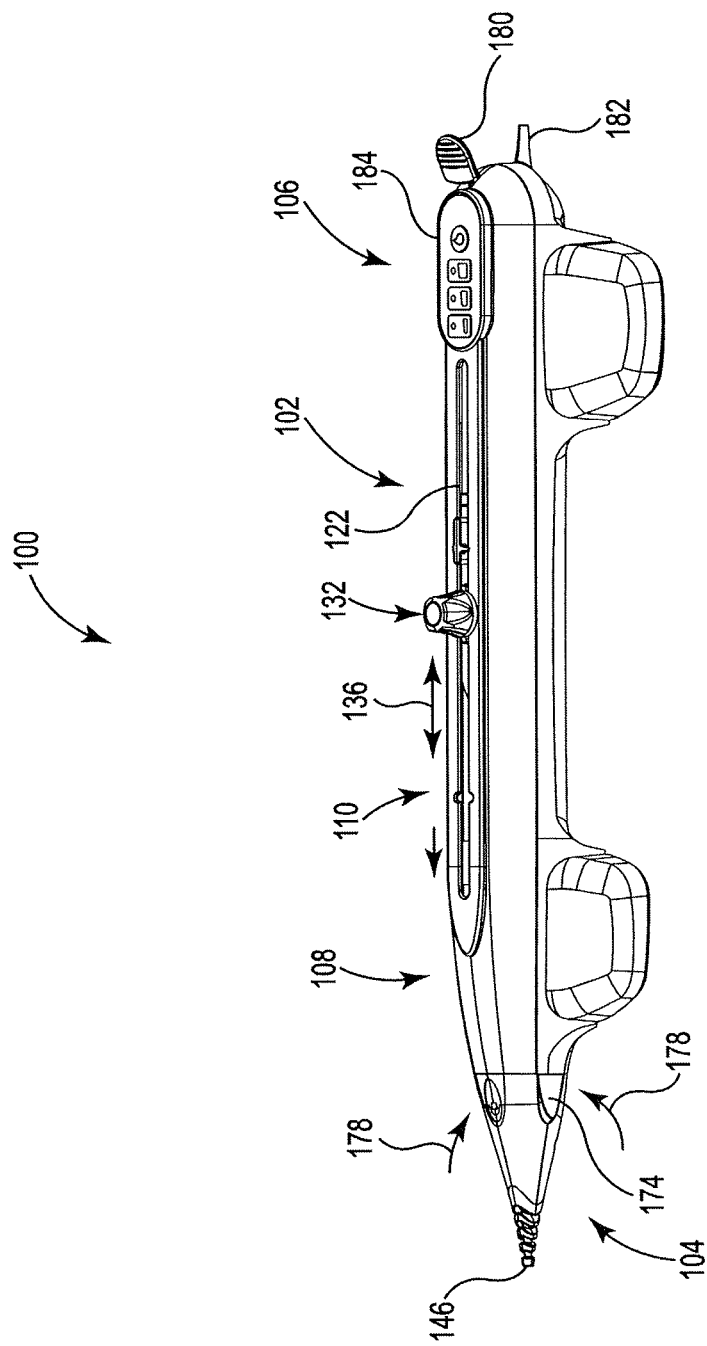
FIG. 1A is a perspective view of an embodiment of a rotational atherectomy device.

In the following detailed description of the various embodiments illustrated in the appended figures, like components and elements are identified using like reference numerals.

Figure 1B:
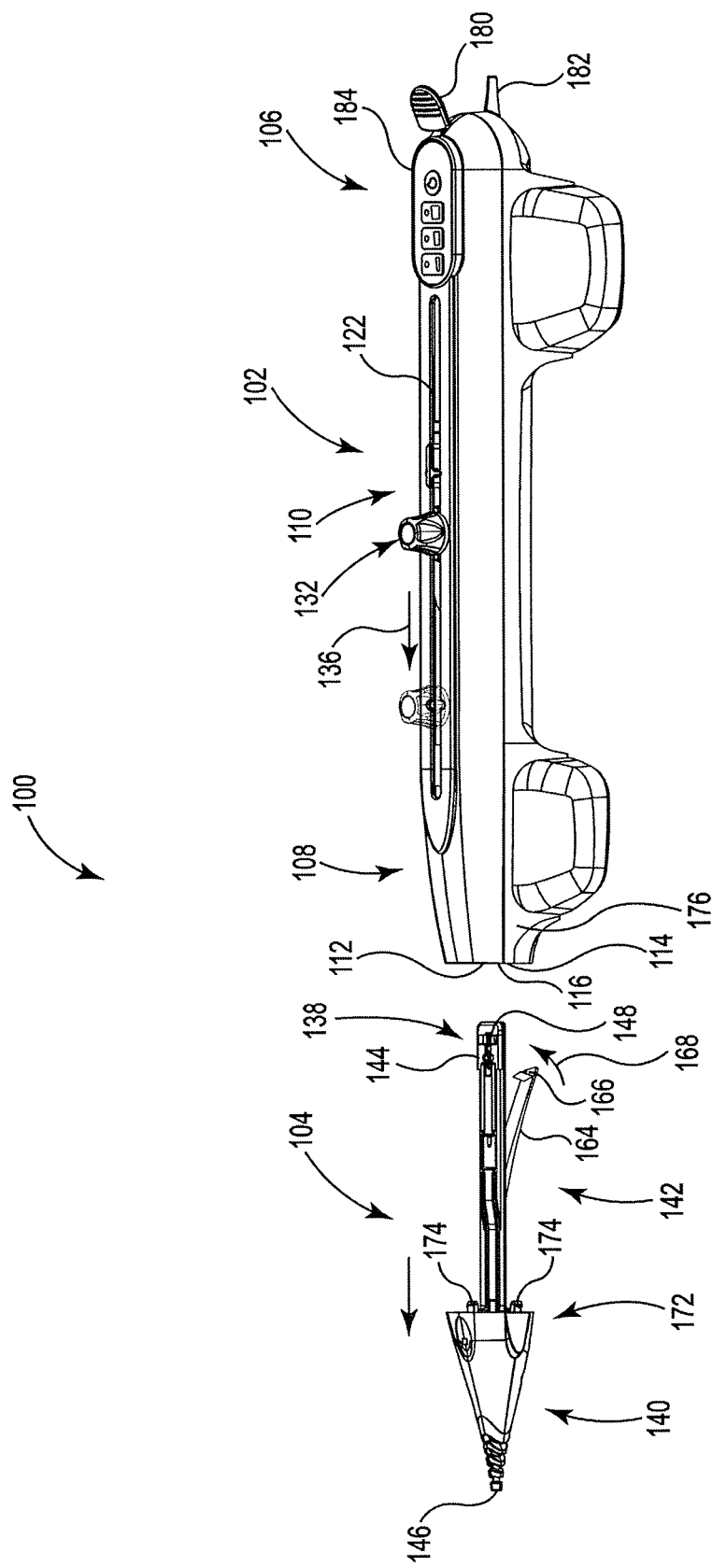
FIG. 1B illustrates the device of FIG. 1A in an unloaded state.
Figure 1C:
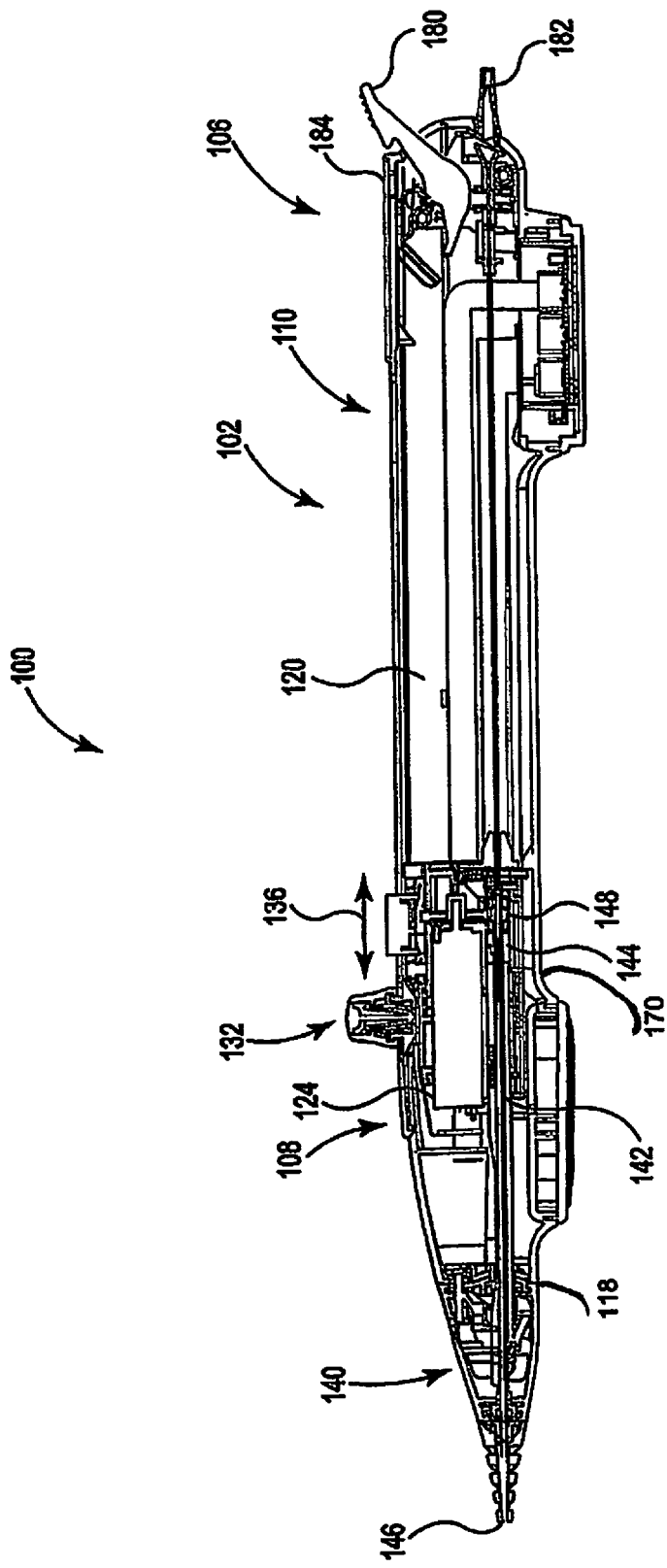
FIG. 1C is a longitudinal cross-sectional view of the device of FIG. 1A.

FIGS. 1A and 1B, respectively, are perspective views of an embodiment of a rotational atherectomy device 100 in a "loaded" and an "unloaded" state, and FIG. 1C is a longitudinal cross-sectional view the device 100 in the "loaded" state. The device 100 includes a handle 102 and an exchangeable drive shaft cartridge 104 that can be removably connected to one another. The device 100 is considered to be in the "loaded" state when the handle 102 and the drive shaft cartridge 104 are connected to one another, and is considered to be in the "unloaded" state when the handle 102 and the drive shaft cartridge 104 are separated from one another. The drive shaft cartridge 104 is referenced as "exchangeable" because the device 100 is configured for enabling an operator to use different drive shaft cartridges with the same handle 102.

In some embodiments, the handle 102 includes a proximal section 106, a distal section 108, and an elongated hollow intermediate section 110 extending between the proximal and distal sections 106 and 108, respectively. In some embodiments, the distal section 108 includes a channel 112 extending proximally from an opening 114 in a distal end 116 of the handle 102. The channel 112 and the opening 114 are configured for passage therethrough of at least a portion of the drive shaft cartridge 104. The intermediate section 110 includes an opening 118 between a longitudinally extending interior 120 of the intermediate section 110 and the channel 112 in the distal section 108. The opening 118 is also configured for passage therethrough of at least a portion of the drive shaft cartridge 104. The intermediate section 110 further includes a longitudinally extending slot 122 extending into the interior 120.

The interior 120 is configured for housing and for the longitudinal displacement therewithin of a prime mover carriage 124. As further described elsewhere with reference to FIGS. 2A and 2B, the prime mover carriage 124 includes a prime mover 126 having a prime mover gear 128 fixedly attached to a shaft 130 of the prime mover 126. In some embodiments, the prime mover 126 is a turbine that can be operated using a variety of means including fluids such as liquid and compressed gas. In other embodiments, the prime mover 126 is an electric motor that can be operated using a variety of electrical sources including an alternate current (AC) source and a direct current (DC) source.

The device 100 further includes at least one control knob 132 having a portion 134 extending through the slot 122 and operationally coupled to the prime mover carriage 124. Accordingly, a longitudinal displacement of the control knob 132 as indicated by the arrow 136 will induce a longitudinal displacement of the prime mover carriage 124, and the prime mover 126 included therewith. In some embodiments, a position of the prime mover carriage 124 within the intermediate section 110 can be fixed or locked, as needed, using the control knob 132. For instance, the control knob 132 can be operated into a locked state for inhibiting the longitudinal displacement of the control knob 132 and of the prime mover carriage 124 coupled thereto. The longitudinal displacement of the control knob 132, and of the prime mover carriage 124 coupled thereto, can be enabled or permitted by operating the control knob 132 into an unlocked state. In some embodiments, the locked and unlocked state are attained by rotating the control knob 132. In alternate embodiments, the control knob 132 can be operated in a different manner for providing the described functionality. In other embodiments, alternative configurations can be included for fixing or locking the position of the prime mover carriage 124, wherein the control knob 132, or some other means, is used for the longitudinal displacement of the prime mover carriage 124. All alternatives as may become apparent to those having ordinary skill in the art are considered as being within the metes and bounds of the instant disclosure.

Figure 1D:
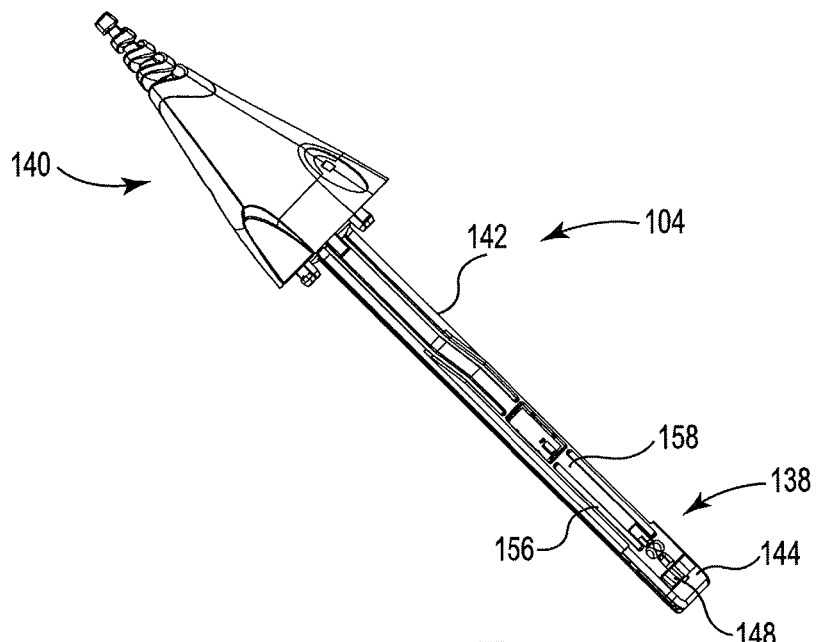
FIG. 1D is a perspective view of an embodiment of an exchangeable drive shaft cartridge for the device of FIG. 1A.

FIG. 1D is a perspective view of an embodiment of the exchangeable drive shaft cartridge 104. As illustrated, the exchangeable drive shaft cartridge 104 includes a proximal section 138, a distal section 140, a drive shaft 142, and a gear engagement assembly 144. The drive shaft 142 includes a proximal end and a distal end, and extends through an opening 146 in the distal section 140. In some embodiments, the opening 146 is through a distal end of the drive shaft cartridge 104. However, this is neither required or necessary. For instance, in alternate embodiments, the drive shaft 142 can extend through an opening in a side of the distal section 140. The gear engagement assembly 144 includes a drive shaft gear 148 fixedly attached to the proximal end of the drive shaft 142 such that rotating the drive shaft gear 148 will rotate the drive shaft 142.

In some embodiments, the prime mover gear 128 and the drive shaft gear 148 can be removably meshed (or engaged). As such, when the gears are meshed, operating the prime mover 126 will induce a rotational movement in the prime mover gear 128, the drive shaft gear 148 and the drive shaft 142. The rotational movement of the drive shaft 142 can be stopped by un-meshing (or disengaging) the prime mover gear 128 and the drive shaft gear 148 and/or by stopping the prime mover 126. As will be apparent to those having ordinary skill in the art, the rotational speed of the drive shaft 142 will be determined at least in part by the gear ratio of the drive shaft gear 148 to the prime mover gear 128 and by the rotational speed of the prime mover 126. In certain embodiments, the prime mover gear 128 and the drive shaft gear 148 are substantially similar in that they are of the same diameter and have the same number of teeth. In such embodiments, the prime mover gear 128 and the drive shaft gear 148 will have substantially similar rotational speeds. In other embodiments, the prime mover gear 128 and the drive shaft gear 148 can have different rotational speeds such that one of the two meshed gears rotates faster or slower than the other. As will be apparent to those having ordinary skill in the art, this can be accomplished by decreasing the diameter and increasing the number of teeth for one of the two gears relative to the other. While the embodiments describe and illustrate only one prime mover gear 128 and only one drive shaft gear 142, such arrangements and quantities of gears should not be considered as limiting. For instance, although not shown, some embodiments of the device 100 may include a gear box having one or more additional gears meshed with the one prime mover gear 128 and the one drive shaft gear 148.

In some embodiments, the prime mover 126 and the drive shaft 142 are rotatably coupled with a mechanism that can both engage and disengage the prime mover 126 and the drive shaft 142 from one another. In a non-limiting exemplary embodiment, the mechanism is a clutch mechanism, including a magnetic clutch.

In order to use the device 100, it must be "loaded" by connecting the handle 102 and the drive shaft cartridge 104 to one another such that the prime mover gear 128 and the drive shaft gear 148 are meshed. In some embodiments, this is accomplished by inserting at least the gear engagement assembly 144 into the handle 102 and juxtaposing it with the prime mover carriage 124.

The channel 112 and the openings 114 and 118 are configured for passage therethrough of at least the gear engagement assembly 144. The gear engagement assembly 144 is inserted into the opening 114, advanced through the channel 112 and the opening 118, and into the interior 120 of the intermediate section 110. Thereafter, the prime mover carriage 124 and the gear engagement assembly 144 are advanced towards one another, either in combination or individually one towards the other, until the prime mover gear 128 and drive shaft gear 148 are aligned with one another. In some embodiments, before the gear engagement assembly 144 is advanced through the opening 118, the prime mover carriage 124 is displaced towards the opening 118 and held thereat by operating the control knob 132 to its locked state. Thereafter, the gear engagement assembly 144 is advanced through the opening 118 until the prime mover gear 128 and drive shaft gear 148 are aligned with one another.

For ensuring alignment of the prime mover gear 128 and drive shaft gear 148, some embodiments of the device 100 include at least one alignment element for guiding at least the gear engagement assembly 144. In some embodiments of the device 100, at least a portion of an alignment element is provided in one or more of the channel 112, the openings 114 and 118, the interior 120, the prime mover carriage 124, and the gear engagement assembly 144. In certain embodiments of the device 100, the alignment element can include at least a first and a second complementary section, wherein the first section is disposed on the gear engagement assembly 144 and the second section is disposed on any one or more of the channel 112, the openings 114 and 118, the interior 120, and the prime mover carriage 124. For instance, the alignment element may include a tongue-and-groove configuration, wherein the first section, i.e., the tongue, is disposed on the gear engagement assembly 144 and the second section, i.e., the groove, is contiguously or sectionally (e.g., piece-wise) disposed on one or more of the channel 112, the openings 114 and 118, the interior 120, and the prime mover carriage 124. Of course, the components or elements of the device 100 on which the tongue and the groove are disposed can be reversed. It should be appreciated that it is not always necessary or a requirement that the alignment element include both a first and a section. In some embodiments, the components and/or elements of the device 100 can be configured such that only one section of the alignment element is required. Some non-limiting examples for the alignment element include one or more ramps, ribs, rails, and channels. All alternative configurations for the alignment element as may become apparent to those having ordinary skill in the art are considered as being within the metes and bounds of the instant disclosure.

Figure 2C:
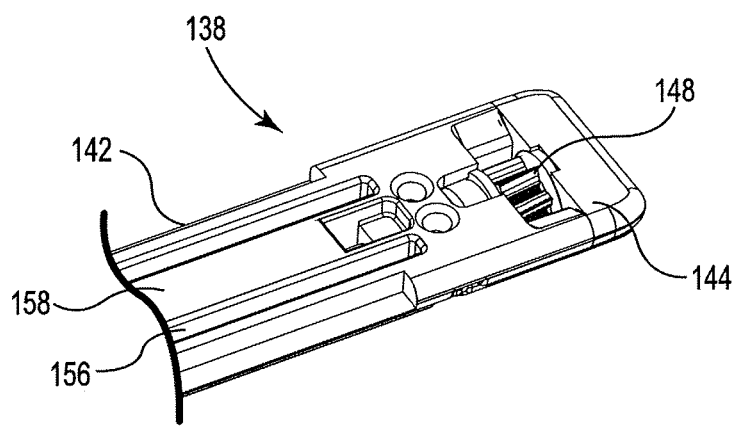
FIG. 2C is a detailed perspective view of a proximal section of the exchangeable drive shaft cartridge of FIG. 1D.
Figure 2A:
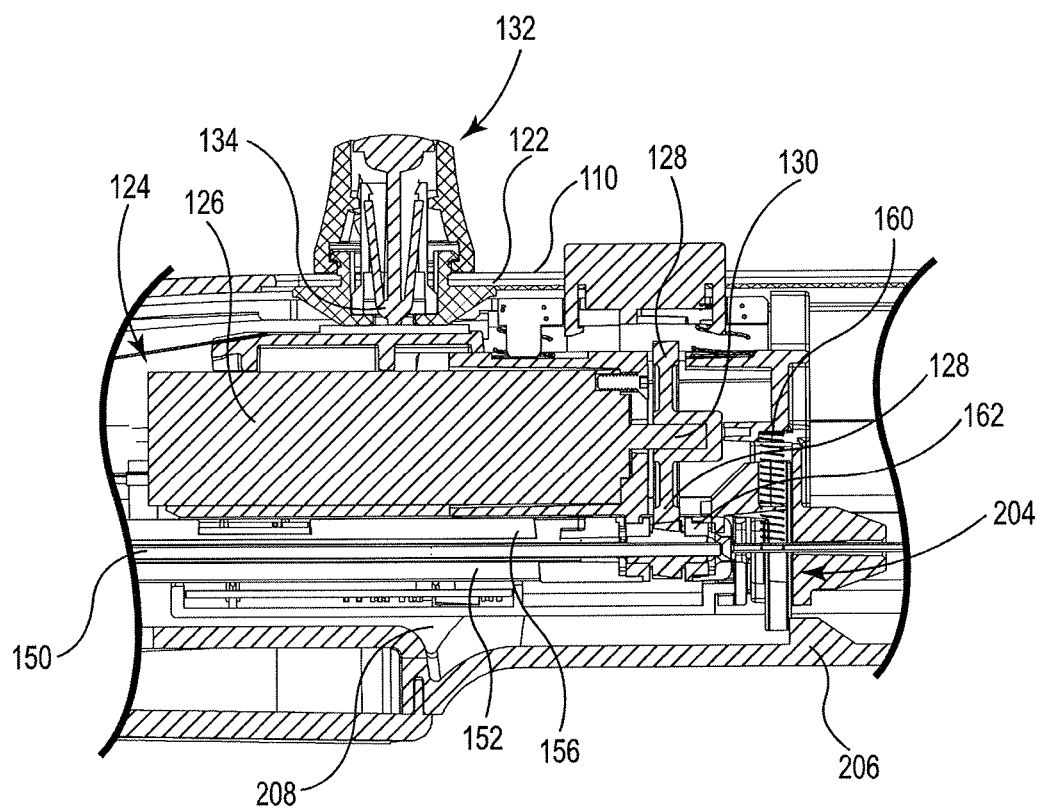
FIG. 2A is a detailed longitudinal cross-sectional view of an embodiment of a prime mover carriage within the unloaded device of FIG. 1B.
Figure 2B:
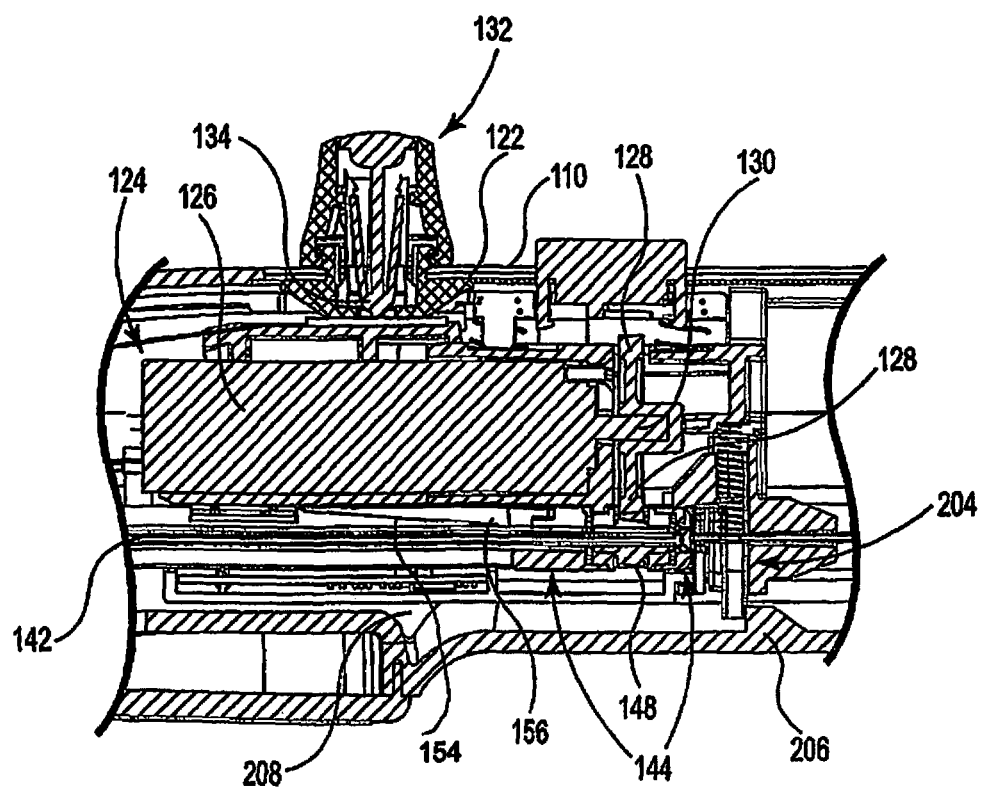
FIG. 2B is a detailed longitudinal cross-sectional view of the prime mover carriage of FIG. 2A with the exchangeable drive shaft cartridge of FIG. 1D attached thereto.

A non-limiting exemplary embodiment of an alignment element having first and second complementary sections is illustrated in FIGS. 2A-2C. FIG. 2A is a detailed cross-sectional view illustrating a state of the prime mover carriage 124 without the gear engagement assembly 144 attached thereto; FIG. 2B is a detailed cross-sectional view illustrating a state of the prime mover carriage 124 with the gear engagement assembly 144 attached thereto; and FIG. 2C is a close-up perspective view of the proximal section 138 of the drive shaft cartridge 104. In the illustrated embodiment, the alignment element includes a first and a second section. The first section, disposed on the prime mover carriage 124, is defined at least in part by an insertion channel 150. In some embodiments, the insertion channel 150 is defined at least in part by first and second guides 152 and 154, respectively. In some embodiments, the second guide 154 is defined at least in part by a ramped planar surface having a thickness that increases from a distal end to a proximal end of the second guide 154. The second section of the alignment element, illustrated in FIG. 2C, is disposed on at least the proximal section 138 of the drive shaft carriage 104. In the illustrated embodiment, the second section is defined at least in part by one or more indents 156, 158 configured for slidable engagement with one or both of the first and second guides 152 and 154.

In some embodiments, the device 100 includes at least one biasing element for meshing the aligned prime mover gear 128 and the drive shaft gear 154 such that when the gears are meshed, a rotational movement of one of the prime mover 126 and the drive shaft 142 will induce a rotational movement in the other. In some embodiments, the at least one biasing element displaces at least the prime mover gear 126 towards a location whereat the drive shaft gear 142 will be positioned when the gears 126 and 142 are aligned. In other embodiments, the at least one biasing element displaces at least the drive shaft gear 142 towards a location whereat the prime mover gear 126 will be positioned when the gears 126 and 142 are aligned. In alternate embodiments, the device 100 can include one or more biasing elements configured for displacing both the prime mover gear 126 and the drive shaft gear 142 towards one another when the gears 126 and 142 are aligned. Non-limiting examples of biasing elements include compression springs, coil springs, leaf springs, and other suitable components and/or materials.

FIGS. 2A and 2B illustrate a non-limiting exemplary embodiment of the device 100 having a spring 160 biasing element configured for biasing at least the prime mover gear 128 towards the drive shaft gear 148. When the device 100 is not loaded and/or the prime mover carriage 124 and the gear engagement assembly 144 are not juxtaposed, the spring 160 pushes at least the prime mover gear 128 towards the location whereat the drive shaft gear 148 will be positioned when the gears 128 and 148 will be aligned when the device 100 is loaded. The alignment element is configured for inhibiting or minimizing roll, pitch and yaw of the gear engagement assembly 144 and the prime mover carriage 124 as they are advanced towards one another when loading the device 100. As the leading edge of the gear engagement assembly 144 enters the insertion channel 150 and the prime mover gear 128 and the drive shaft gear 148 advance towards each other, the ramped planar surface of the second guide 154 causes the proximal section of the prime mover carriage 124, and at least the prime mover gear 128, to move in a direction away from the advancing drive shaft gear 148. When the prime mover carriage 124 and the gear engagement assembly 144 are appropriately juxtaposed, the prime mover gear 128 and the drive shaft gear 148 will be aligned, and the gears 128 and 148 will mesh because of the biasing force from the spring 160. While only one spring 160 is illustrated and described with reference to the FIGS. 2A and 2B, it should be readily apparent that more than one spring can be used for providing the required functionality. Accordingly, all such alternatives are considered as being within the metes and bounds of the instant disclosure.

In some embodiments, the prime mover carriage 124 includes one or more alignment pins 162 and the gear engagement assembly 144 includes one or more correspondingly aligned apertures configured for receiving the one or more alignment pins 162. The one or more alignment pins 162 and the one or more apertures are configured and located such that when the prime mover carriage 124 and the gear engagement assembly 144 are properly juxtaposed, the prime mover gear 128 and the drive shaft gear 148 will be aligned as required, and the one or more alignment pins 162 and the corresponding aperture will engage. Accordingly, further relative displacement of the prime mover carriage 124 and the gear engagement assembly 144 will be inhibited and the alignment of the gears 128 and 148 will be maintain. Spring forces from the one or more biasing elements will mesh the prime mover gear 128 and the drive shaft gear 148.

In some embodiments, the drive shaft cartridge 104 includes a releasable locking feature that engages with a releasable locking feature on at least one of the handle 102 and the prime mover carriage 124. In some embodiments, a self-releasing locking mechanism 204 is provided at or near the proximal end of the prime moving carriage 124. In the embodiment shown, the self-releasing locking mechanism 204 is positioned proximal of the prime mover gear 128. In some embodiments, at least a portion of the proximal section 138 of the drive shaft cartridge 104 is engaged with the self-releasing locking mechanism 204. In some embodiments, the handle 102 also has a self-releasing locking mechanism 206 within channel 208. In certain embodiments, the one or more self-releasing locking mechanisms 204 and 206 are configured for inhibiting the displacement or movement of the prime mover carriage 124 while it is not connected with the drive shaft cartridge 104. When the device 100 is "loaded" and the prime mover gear 128 and the drive shaft gear 148 are meshed, the one or more self-releasing locking mechanisms 204 and 206 is disengaged.

FIG. 1B illustrates an alternate embodiment of an elongated biasing element 164 that may also be used as an alignment element. The biasing element 164 includes a distal end fixedly or removably attached to or integrally formed with the drive shaft cartridge 104 at a location distal from the gear engagement assembly 144. In certain embodiments, the biasing element 164 extends proximally and is configured such that in the absence of any external force, a proximal end 166 thereof extends away from the gear engagement assembly 144. When appropriate force is applied on at least a portion of the biasing element 164, the proximal end 166 is displaced in the direction indicated by the arrow 168 towards the gear engagement assembly 144 and spring force is stored in the biasing element 164. Then, when the applied force is removed, the stored spring force will urge the proximal end 166 away from the gear engagement assembly 144 in the direction opposite that indicated by the arrow 168.

Additionally, in some embodiments, the biasing element 164 can be configured as the first section of an alignment element, and the second section of the alignment element can be disposed on at least a portion of the handle 102. The second section can be a groove or similar structure configured for slidable engagement with the biasing element 164. In some embodiments, the second element is disposed on, e.g., integrally formed with, the prime mover carriage 124. Additionally, or in the alternative, at least a portion of the handle 102 distal from the prime mover carriage 124 can include the second section of the alignment element. For example, the second section can be disposed on at least one or more of the opening 114 in the distal end 116 of the handle 102, portions of or the entire channel 112 extending proximally from the opening 114, the opening 118 in the intermediate section 110, and at least a portion of the interior 120 proximal of the opening 118.

In some embodiments, the second section of the alignment element can include an indent 170 configured for removably receiving the proximal end 166 of the biasing element 164 and inhibiting further displacement of the drive shaft cartridge 104 in the proximal direction within the handle 102. In particular, the displacement of the gear engagement assembly 144 in the proximal direction within the handle 102 is inhibited. Accordingly, it should be readily apparent that the proximal end 166 and the indent 170 must have complementary configurations such that the prime mover gear 128 and the drive shaft gear 148 are aligned when the proximal end 166 is removably received within the indent 170. For loading the device 100, the proximal end 166 and the gear engagement assembly 144 are displaced towards one another and both are then inserted through the opening 114 into the handle 102. The gear engagement assembly 144 and the prime mover carriage 124 are displaced towards one another until the proximal end 166 of the biasing element 164 is removably received within the indent 170. The prime mover gear 128 and the drive shaft gear 148 will be aligned with one another, and the spring force stored within the biasing element 164 will cause the gears 128 and 148 to mesh.

Some embodiments of the device 100 can include one or more release mechanisms for separating, e.g., un-meshing, the meshed gears 126 and 142 so that the exchangeable drive shaft cartridge 104 can be removed from the handle 102. In other embodiments of the device 100, one or more of the handle 102, the drive shaft cartridge 104 and the alignment element can be configured such that a displacement of the handle 102 and the drive shaft cartridge 104 away from one another will separate the juxtaposed prime mover carriage 124 and the gear engagement assembly 144 and also separate, e.g., un-mesh, the meshed gears 126 and 142.

Figure 3A:
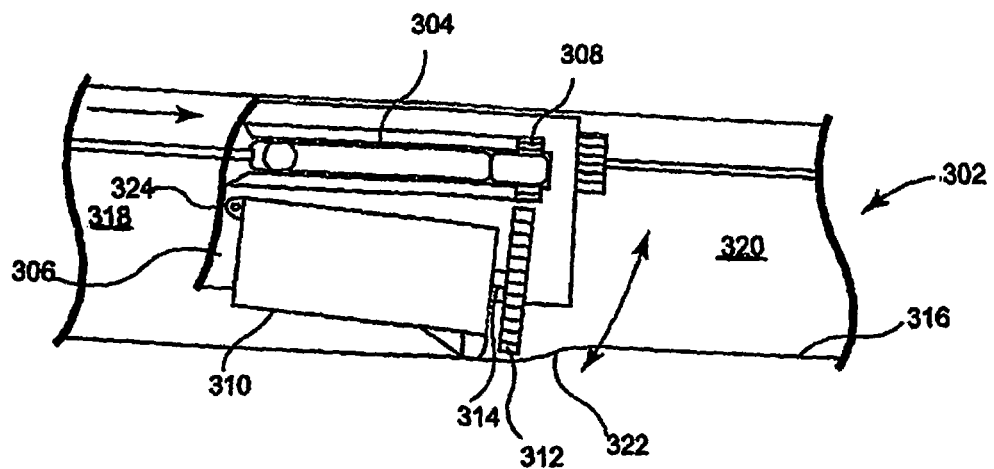
FIG. 3A is a longitudinal cross-sectional view illustrating embodiments of a prime mover carriage and a gear engagement assembly in an un-meshed state.
Figure 3B:
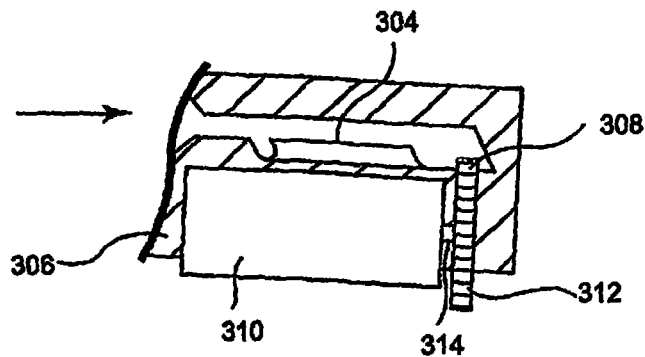
FIG. 3B is a longitudinal cross-sectional view illustrating the prime mover carriage and the gear engagement assembly of FIG. 3A in a un-meshed state.

FIGS. 3A and 3B are partial side views of an embodiment for meshing the prime mover gear 128 and the drive shaft gear 148 with one another in an embodiment of the device 100. As described elsewhere, embodiments of the devices disclosed herein, e.g., device 100, include a handle defined at least in part by an elongated hollow intermediate section. FIG. 3A illustrates a portion of an interior 302 within an embodiment of an elongated hollow intermediate section of a handle, e.g., handle 102. As with interior 120, the interior 302 is configured for housing and for a linear displacement of a gear engagement assembly 304 and a prime mover carriage 306. In several respects the embodiments of the gear engagement assembly 304 and of the prime mover carriage 306, respectively, are substantially similar to the gear engagement assembly 144 and the prime mover carriage 124 described elsewhere with reference to the device 100. As such, the gear engagement assembly 304 includes a drive shaft gear 308 fixedly attached to a proximal end of a drive shaft extending distally therefrom. And, the prime mover carriage 306 includes a prime mover 310 having a prime mover gear 312 fixedly attached to a shaft 314 thereof.

As shown, the interior 302 includes a guide rail 316 extending through at least a portion thereof. In some embodiments, the guide rail 316 divides the interior 302 into at least a first section 318 and a second section 320. As illustrated, the first section 318 is configured for accommodating the gear engagement assembly 304 and the prime mover carriage 306 while the drive shaft gear 308 and the prime mover gear 312 are aligned with one another but are not meshed. The second section 320 is configured for accommodating the gear engagement assembly 304 and the prime mover carriage 306 after the drive shaft gear 308 and the prime mover gear 312 are meshed. The guide rail 316 further includes a transition section 322 extending between the first and the second sections 318 and 320, respectively. In some embodiments, the transition section 322 is configured for advancing at least the aligned drive shaft gear 308 and the prime mover gear 312 towards one another while the gear engagement assembly 304 and the prime mover carriage 306 are displaced, either singularly or in combination, from the first section 318 into the second section 320. As will be apparent, the transition section 322 is therefore configured for meshing the aligned drive shaft gear 308 and the prime mover gear 312 when they are displaced from the first section 318 into the second section 320. In the illustrated embodiment, while the gear engagement assembly 304 and the prime mover carriage 306 are together displaced from the first section 318 into the second section 320, the transition section 322 causes the prime mover carriage 306 to pivot about a pivot point 324 such that at least the prime mover gear 312 is displaced towards, and meshed with, the drive shaft gear 308. In some embodiments, reversing the displacement of the gear engagement assembly 304 and the prime mover carriage 306 from the second section 320 into the first section 318 will un-mesh the drive shaft gear 308 and the prime mover gear 312 from one another. The drive shaft cartridge of which the gear engagement assembly 304 is a component of, can be removed from the handle and replaced with a different or another similar drive shaft cartridge having a gear engagement assembly substantially similar to the gear engagement assembly 304.

In the first section 318 of the embodiment illustrated in FIG. 3A, the prime mover carriage 306 is shown tilted about the pivot point 324 such that the drive shaft gear 308 and the prime mover gear 312 are separated from, and not meshed with, one another. In some embodiments, the illustrated tilting of the prime mover carriage 306 may be due to gravitational forces. Although not shown, other embodiments can include one or more biasing elements configured to tilt the prime mover carriage 306 as illustrated. Non-limiting exemplary biasing elements include coiled springs, leaf springs and similar components configured to store spring forces when displace from their "normal" state. For instance, one or more coil springs, each having a compressed state as its "normal" state, may be provided whereby, in the first section 318, the prime mover carriage 306 is tilted as illustrated in FIG. 3A. Displacing the prime mover carriage 306, with the gear engagement assembly 304, into the second section 320, as illustrated in FIG. 3B, will "stretch" the one or more springs and store spring forces therewithin. The subsequent displacement of the prime mover carriage 306, with the gear engagement assembly 304, from the second section 320 into the first section 318 will "release" the spring forces whereby the prime mover carriage 306 will tilt as illustrated in FIG. 3A, and the drive shaft gear 308 and the prime mover gear 312 will un-mesh, i.e., separate from one another.

In order to use the device 100, the distal section 108 of the handle 102 and the distal section 140 of the drive shaft cartridge 104 need be coupled to one another such that during use, the prime mover gear 128 and the drive shaft gear 148 remain meshed with one another within the handle 102. To that end, embodiments of the device 100 may include one or more connectors and associated release mechanisms, respectively, configured for engaging and separating or disengaging the handle 102 and the drive shaft cartridge 104 from one another. As stated, such coupling needs to be releasable because it may be desirable or necessary to replace the drive shaft cartridge 104 during the procedure. Accordingly, some embodiments of the one or more connectors include complementary first and second sections that can be integrally formed, respectively, with the distal section 108 of the handle 102 and with the distal section 140 of the drive shaft cartridge 104. The first and second sections are configured for being removably coupled to each other. It will be readily apparent to one skilled in the art that the component on which the first and the second sections are formed can be reversed without affecting the required functionality. In other words, the functionality of the connector will not change if the first section is integrally formed with the distal section 140 of the drive shaft cartridge 104 and the second section integrally formed with the distal section 108 of the handle 102.

FIGS. 1A and 1B illustrate an embodiment of a connector configured for keeping the handle 102 and the drive shaft cartridge 104 connected to one another while the device 100 is in use. The connector includes a tabbed connector 172 integrally formed with the distal section 140 of the drive shaft cartridge 104 and one or more complementary holes 176 integrally formed with the distal section 108 of the handle 102. The tabbed connector 172 includes one or more tabs 174, each of which removably engages with a complementary hole 176 in the distal section 108. When the device 100 is "loaded," i.e., the distal sections 108 and 140 abut one another, the tabbed connector 172 prevents separation of the handle 102 and the drive shaft cartridge 104 while the device 100 is in use during a procedure. For "unloading" the device 100, i.e., separating the handle 102 and the drive shaft cartridge 104 from one another, the distal sections 108 and 140 can be disengaged from one another by applying pressure to the tabs 174 in the direction indicated by the arrows 178, and displacing the distal sections 108 and 140 away from one another.

In some embodiments, when the exchangeable drive shaft cartridge 104 is loaded, and the prime mover gear 128 and the drive shaft gear 148 are properly meshed and engaged with one another, a gap may exist between the distal section 140 of the drive shaft cartridge 104 and the distal end 116 of the handle 102. In some embodiments, the one or more connectors for removably connecting the distal end 116 of the handle 102 and the distal section 140 of the drive shaft cartridge 104 with one another can include a sealing mechanism for creating a sealed coupling therebetween.

Alternate exemplary embodiments of one or more connectors and associated release mechanisms includes snap-fit connectors, tongue and groove connectors, rails, rotatable connectors, bayonet mounts and ribs. For instance, in a non-limiting exemplary embodiments, the sealing mechanism (i.e., the one or more connectors) can be a bayonet mount wherein a rotational displacement of the handle 102 and/or the drive shaft cartridge 104 in opposite directions, after being juxtaposed, connects or disconnects the handle 102 and the drive shaft cartridge 104 from one another.

In some embodiments, the one or more connectors for removably connecting the handle 102 and the drive shaft cartridge 104 with one another is also configured to function as a seal. For example, the one or more connectors can also form a fluidic seal that inhibits any flow of fluid therethrough.

Other embodiments of one or more release mechanisms as may become apparent to those having ordinary skill in the art are considered as being within the metes and bounds of the instant disclosure.

As illustrated in FIGS. 1A-1C, the device 100 includes a guide wire clamp or brake 180 in the proximal section 106 of the handle 102. Engaging the guide wire clamp or brake 180 enables the user of the device 100 to stop the insertion or retraction of a guide wire 182 extending through the device 100. When the guide wire clamp or brake 180 is operated to its dis-engaged state, the guide wire 182 can then be inserted or retracted.

In some embodiments, the proximal section 106 of the handle 102 includes at least one control panel 184 through which the user can monitor and/or control the operation of the device 100. Some embodiments of the at least one control panel 184 enable the user of the device 100 to start, stop, change and monitor the rotational speed of the prime mover 126 which affects the rotational speed of the drive shaft 142. Certain embodiments of the at least one control panel 184 enable the user of the device 100 to monitor and/or control the flow of saline. Some embodiments of the device 100 may include one or more fiber optic cables extending into the vasculature of a patient. In such embodiments of the device 100, the at least one control panel 184 may be configured for displaying visuals, e.g., images, of the interior of the vasculature. Certain embodiments of the device 100 may include one or more sensors for sensing conditions such as whether or not the handle 102 and the drive shaft cartridge 104 are properly coupled as required for operating the device 100. The one or more sensors may also include means for sensing parameters such as the environmental conditions (e.g., temperature, pressure, etc.) within the vasculature and/or the physical conditions (e.g., thickness, pliability, etc.) of the vasculature. Accordingly, some embodiments of the at least one control panels 184 may be configured for displaying the sensed conditions. Certain embodiments of the at least one control panels 184 may include at least a micro-processor, memory, display interfaces, input/output ports or interfaces, etc. All functionalities of the at least one control panel 184 as may become apparent to those having ordinary skill in the art are considered as being within the metes and bounds of the instant disclosure.

As described elsewhere, certain embodiments of the device 100 include one or more sensors for detecting whether or not the handle 102 and the drive shaft cartridge 104 are properly connected. More specifically, the one or more sensors are configured to detect whether or not the distal end 116 of the handle 102 and the proximal end of the distal section 140 are properly connected. If proper connection as required for operating the device 100 is not detected, the drive shaft 142 may be inhibited from advancing and/or rotating. This is also applicable for embodiments wherein the drive shaft 142 is configured as a telescoping drive shaft as illustrated in FIG. 1E.

In some embodiments of the device 100, the distal section 140 of the drive shaft cartridge 104 includes a nosecone 186. In embodiments of the device 100 wherein the drive shaft 142 is telescoping, the nosecone 186 and the drive shaft cartridge 104 are configured for being removably attached to one another. FIG. 1F illustrates an embodiment wherein the nosecone 186 includes a proximally extending structure 188 and the drive shaft cartridge 104 includes an output gear hypotube 190. As shown, a proximal section 192 of the structure 188 and a distal section 194 of the hypotube 190 include complementary elements 196 and 198, respectively, configured for removably connecting the structure 188 and the hypotube 190 with one another. In some embodiments, the complementary elements 196 and 198 respectively include a spring-biased tab and an indent configured for slidable engagement with one another. In certain embodiments, the spring-biased tab is configured as a leaf spring. In other embodiments, the complementary elements 196 and 198 respectively include a spring-biased ball and a depression configured for slidable engagement with one another. Of course, the configurations of the complementary elements 196 and 198 can be reversed. Furthermore, the described and illustrated embodiments are exemplary and, as such, should not be construed as being limiting. Modifications or alternate embodiments for removably connecting the nosecone 186 and the hypotube 190 are considered as being within the metes and bounds of the instant disclosure.

In use, when the drive shaft 142 is in the retracted state and not telescoping, the structure 188 and the hypotube 190 are connected or coupled to one another at their respective proximal and distal sections 192 and 194. In some embodiments, the device 100 must be "loaded" in order to telescope the drive shaft 142. If the device 100 is "unloaded", one or more locking mechanisms (not shown) inhibit the drive shaft 142 from being telescoped. When the device 100 is "loaded", the one or more locking mechanism(s) are disengaged, and the drive shaft 142 can be telescoped by displacing the nosecone 186 and the handle 102 in opposite directions away from each other.

In certain embodiments, the structure 188 and the hypotube 190 include complementary alignment elements for aiding the insertion of the proximal section 192 into the distal section 194. In the illustrated embodiment, the hypotube 190 includes an outwardly flaring distal end 200, and the structure 188 includes an inwardly tapering proximal end 202. The described embodiment should not be construed as being limiting. In alternate embodiments, the distal section 194 of the hypotube 190 can be configured for insertion into and retraction from the proximal section 192 of the structure 188.

Certain embodiments of the device 100 include a saline infusion port in fluid communication with a saline reservoir. The device may further include an internal saline tube configured for transporting the saline from the infusion port to an inner lumen of a catheter. As such, the saline from the reservoir may be used for reducing friction between the rotating drive shaft 142 and any non-rotating components disposed within and/or around the drive shaft 142. The saline from the reservoir may also be used as a heat transfer fluid.

Figure 4A:
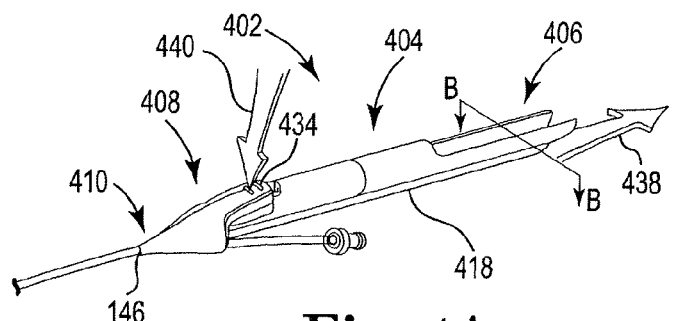
FIG. 4A is a perspective view of a distal section in an embodiment of an exchangeable drive shaft cartridge for another embodiment of a rotational atherectomy device.

FIG. 4A is a perspective view of a distal section 402 in an embodiment of an exchangeable drive shaft cartridge for another embodiment of a rotational atherectomy device. The distal section 402 includes a tubular section 404 having a trough 406 extending proximally therefrom, and a tubular nosecone 408 extending distally therefrom. The tube of the tubular section 404 is contiguous at its first open end with the trough 406, and is contiguous at its second open end, opposite the first open end, with a first open end of the tube of the nosecone 408. A second open end, opposite the first open end, of the tube of the nosecone 408 defines the opening 146 in a distal end 410 of the distal section 402. As such, the distal section 402 is configured for passage therethrough of the drive shaft 142 fixedly attached at its proximal end to the drive shaft gear 148 and having a distal end configured for insertion into a vasculature of a patient. While the distal section 402 is illustrated as having a generally circular cross-section throughout, the geometrical shape should not be considered as a requirement and/or limiting. Alternate shapes extending the entire distal section 402 and/or on portions thereof are considered as being within the metes and bounds of the instant disclosure.

Figure 4B:
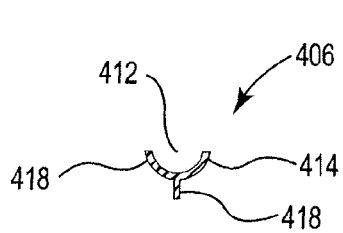
FIG. 4B is a cross-section view of a portion of the distal section of FIG. 4A.

FIG. 4B is a cross-section view of the trough 406 along a plane extending through the sectional line B-B shown in FIG. 4A. In the illustrated embodiment, the trough 406 has a generally U-shaped geometry having a channel 412 defined at least in part by opposing walls 414 and 416. However, this specific geometrical shape for the trough 406 should be considered as a requirement and/or limiting. Alternate configurations as may become apparent to those having ordinary skill in the art are considered as being within the metes and bounds of the instant disclosure.

The distal section 402 is illustrated having a longitudinally extending fin 418 on at least a portion thereof. In FIG. 4A, the fin 418 is illustrated as extending along the entire length of the tubular section 404 and the trough 406. However, the longitudinal extent of the fine 418 and/or its location on the external surface of the distal section 402 should not be considered as a requirement and/or limiting. In some embodiments, the fin 418 extends along only portions of the tubular section 404 and/or the trough 406. In certain embodiments, the fin 418, and/or portions thereof, are positioned at one or more locations on the external surface of the distal section 402. All alternative shapes, sizes, locations, etc., for the fin 418, as may become apparent to those having ordinary skill in the art are considered as being within the metes and bounds of the instant disclosure.

Figure 4D:
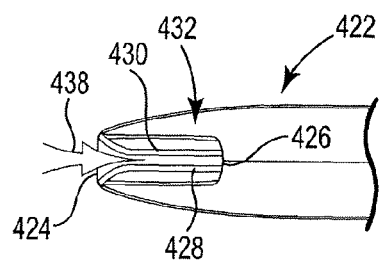
FIG. 4D is a top view of a distal section of the handle of FIG. 4C.
Figure 4C:
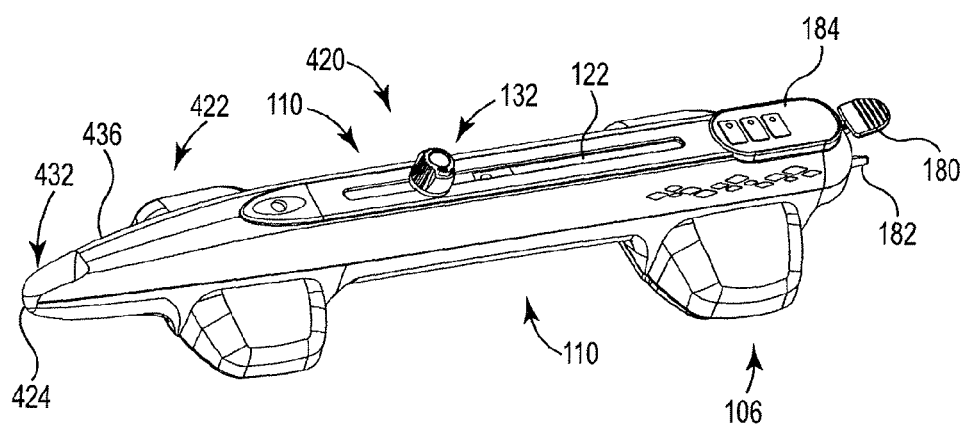
FIG. 4C is a perspective view of a handle configured for removably connecting with the distal section of FIG. 4A.

With reference to FIGS. 4A and 1B, it should be apparent that the respective distal sections 402 and 140 of the drive shaft cartridges are substantially different from one another. Accordingly, the distal sections of the handles through which the drive shaft cartridges having the distal sections 402 and 140 are inserted for removable coupling with the handle also need to be different from one another. FIG. 4C is a perspective view of an embodiment of a handle 420 having a distal section 422 different from the distal section 108 of the handle 102 illustrated in FIG. 1B. In several other aspects, the handles 420 and 102 are substantially similar to one another. A top view of at least a portion of the distal section 422 proximate a distal end 424 of the handle 420 is illustrated in FIG. 4D.

In general, the cross-section of the distal section 422 of the handle 420 through which the drive shaft cartridge is inserted and the cross-section of at least the tubular section 404 of the distal section 402 are complementary and/or substantially similar. As illustrated in FIG. 4D, the distal section 422 includes a channel 426 defined at least in part by opposing guard rails or walls 428 and 430. The channel 426 and the opposing guard rails 428 and 430 extend proximally from an opening 432 in the distal end 424, and are configured for slidable coupling with at least the fin 418, the tubular section 404 and the trough 406 of the distal section 402 of the drive shaft cartridge. In some embodiments, the channel 426 and the opposing guard rails 428 and 430 are configured for aligning the distal sections 402 and 422 with one another.

In some embodiments, the distal end 424 and at least a portion of the distal section 422 proximal thereof is configured for removably connecting with at least a portion of the nosecone 408 of the distal section 402. In certain embodiments, the device includes at least one connector having complementary first and second sections 434 and 436, respectively, disposed on the nosecone 408 and the distal section 422, and configured for connecting and dis-connecting the nosecone 408 and the distal section 422.

For "loading" the device, the gear engagement assembly 144 is inserted through the opening 432 into the handle and is removably connected with the prime mover carriage 124 housed within the interior 120 in the intermediate section 110 of the handle 420. As described elsewhere, the prime mover gear 128 and the drive shaft gear 148 will mesh when the prime mover carriage 124 and the gear engagement assembly 144 are connected with one another. Next, as indicated by the directional arrow 438, the trough 406 and the tubular section 404 of the distal section 402 are inserted into the distal section 422 of the handle 420 through the opening 432. The distal section 402 and at least the distal section 422 of the handle 420 are displaced in opposite directions towards each other until the first and second sections 434 and 436 of the connector engage one another. In the illustrated embodiment, to "unload" the device, for example to change or replace the drive shaft cartridge, the distal section 402 and at least the distal section 422 of the handle 420 are displaced in opposite directions away from each other while concurrently pushing or pressing at least the first section 434 of the connector in the direction indicated by the arrow 440. Concurrently, or subsequently, the gear engagement assembly 144 and the prime mover carriage 124 are disconnected and the gear engagement assembly 144 is removed from the handle 420 through the opening 432.

Figure 5:
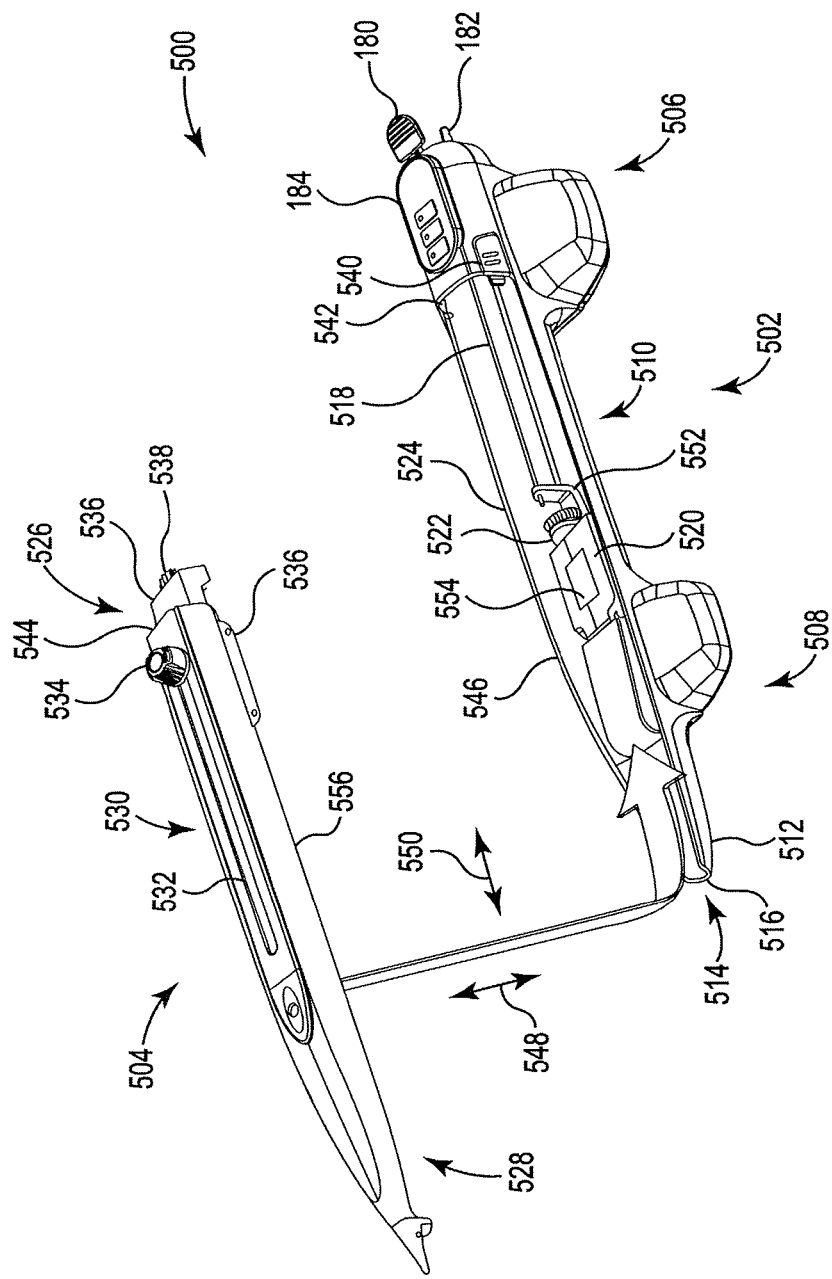
FIG. 5 is a perspective view of another embodiment of a rotational atherectomy device in a dis-assembled state.

FIG. 5 is a perspective view of another embodiment of a rotational atherectomy device 500 in a dis-assembled state. Elements and components of the device 500 that are substantially similar or the same as those in other embodiments of the device are identified with the same reference numerals. The device 500 includes a handle 502 and an exchangeable drive shaft cartridge 504, wherein the handle 502 and the drive shaft cartridge 504 include one or more connectors configured for removably connecting the handle 502 and the drive shaft cartridge 504 to one another.

Some embodiments of the handle 502 include a proximal section 106, a distal section 508, and an elongated intermediate section 510. The distal section 508 includes a channel 512 extending proximally from an opening 514 in a distal end 516 of the handle 502. Certain embodiments of the intermediate section 510 include a trough 518 extending between the proximal and distal sections 106 and 508, respectively, of the handle 502. The trough 518 is configured for housing and longitudinal displacement of a prime mover carriage 520 disposed therewithin. The prime mover carriage 520 includes a prime mover 522 and a prime mover gear 524 fixedly attached to a shaft of the prime mover 522.

Certain embodiments of the drive shaft cartridge 504 include a proximal section 526, a distal section 528, and an intermediate section 530 having a slot 532 extending longitudinally between the proximal and distal sections 526 and 528, respectively. The drive shaft cartridge further includes at least one control knob 534 having at least a portion thereof extending through the slot 532 and operationally coupled to a gear engagement assembly 536. Operationally and functionally, the control knob 534 is substantially similar to the control knob 132 of the device 100. In particular, longitudinal displacement of the control knob 534 along the slot 532 will induce a similar longitudinal displacement of the gear engagement assembly 536. As with the control knob 132, the control knob 534 can be operated between locked and unlocked states. The gear engagement assembly 536 includes a drive shaft gear 538 fixedly attached to a proximal end of a drive shaft extending distally therefrom and through an opening in the distal section 528 of the drive shaft cartridge 504.

In order to use the device 500, the handle 502 and the exchangeable drive shaft cartridge 504 may be removably connected to each other as follows. The control knob 534 is used for proximally displacing the gear engagement assembly 536 and positioning it proximate to and/or within the proximal section 526 of the drive shaft cartridge 504. In some embodiments, such as that illustrated in FIG. 5, the gear engagement assembly 536 may be positioned such that a portion thereof and/or the drive shaft gear 538 extends proximally beyond the proximal end 544. Also as illustrated, the prime mover carriage 520 is located proximate a distal end 546 of the trough 518. The prime mover gear 524 and the drive shaft gear 538 are aligned and then meshed by juxtaposing the prime mover carriage 520 and the gear engagement assembly 536. Concurrently, the handle 502 and the drive shaft cartridge 504 are displaced towards one another until the proximal end 544 of the proximal section 526 (i.e., the drive shaft cartridge 504) and the distal end 542 of the proximal section 506 are removably coupled. Some embodiments of the device 500 may include complementary sections of one or more alignment elements for assisting with and/or maintaining the alignment of the prime mover gear 524 and the drive shaft gear 538. Non-limiting exemplary embodiments of the one or more alignment elements include tongue-and-groove, rails, channels and ribs. Certain embodiments of the device 500 may include complementary sections of one or more connectors for removably coupling the prime mover carriage 520 and the gear engagement assembly 536. Non-limiting exemplary embodiments of the one or more connector include tabbed connectors and snap-fit connectors.

Embodiments of the device 500 include one or more connectors having complementary first and second sections configured for removably coupling (or connecting) the handle 502 and the drive shaft cartridge 504 to each other. Some embodiments of the connector include one or more slidable tabs 540 integrally formed with the proximal section 506 of the handle 502 and complementary tab receptors (not shown) integrally formed with a proximal section 526 of the drive shaft cartridge 504. While FIG. 5 illustrates only one slidable tab 540 at a distal end 542 of the proximal section 506, this should not be construed as being limiting. It should be realized that most embodiments of the device 500 will include one or more additional slidable tabs integrally formed with the proximal section 506 at the distal end 542 thereof. For example, the proximal section 506 may include a slidable tab on the side or wall opposite the side or wall on which the slidable tab 540 is illustratively disposed. Additionally, or in the alternative, the distal end 542 of the proximal section 506 may include a slidable tab integrally formed on the same side or wall on which the control panel 184 is illustratively disposed. Although not shown in FIG. 5, it should be readily apparent that for each of the one or more slidable tabs 540, the drive shaft cartridge 504 will include a complementary tab receptor integrally formed with the proximal section 526 at a proximal end 544 thereof. Of course, it is neither necessary nor a requirement that the one or more connectors include complementary slidable tabs 540 and tab receptors. Alternative configurations of the one or more connectors as may become apparent to those having ordinary skill in the art are considered as being within the metes and bounds of the instant disclosure. For example, the one or more connectors may include snap-fit connectors and tongue and groove connectors.

Some embodiments of the device 500 may include one or more alternative and/or additional connectors having first and second sections configured for removably coupling (or connecting) the handle 502 and the drive shaft cartridge 504 to each other. The handle 502 may be considered as a lower section of the device 500, and the drive shaft cartridge 504 may be considered as an upper section of the device 500. For example, the embodiment of the device 500 illustrated in FIG. 5 includes a first section 546 integrally formed with the distal section 508 of the handle 502, and a complementary second section (not shown) integrally formed with the distal section 528 of the drive shaft cartridge 504. The first and second sections of such connectors are configured for removably coupling at least the distal sections 508 and 528, respectively, of the handle 502 and the drive shaft cartridge 504. In some embodiments, such as that illustrated in FIG. 5, the handle 502 and the drive shaft cartridge 504 are displaced towards one another as indicated by the directional arrow 548, and are thereafter removably coupled by displaced the distal sections 508 and 528 towards one another as indicated by the directional arrow 550. In some embodiments, the connector at the distal section of the device 500 (i.e., in the distal sections 508 and 528) may be further configured as an alignment element such as a tongue-and-groove connector for slidable coupling with or without snap connectors or tab connectors. In certain embodiments, the device 500 may include additional and/or alternative alignment elements and/or connectors, each having complementary first and second sections integrally formed with the longitudinally extending opposing side edges of the handle 502 and the drive shaft cartridge 504. For example, the first sections may be integrally formed with the opposing side edges 552 and 554 of the handle 502, with the complementary second sections, respectively, integrally formed with the opposing side edge 556 and the side edge not shown of the drive shaft cartridge 504. All alternative configurations for the one or more connectors and/or the one or more alignment elements as may become apparent to those having ordinary skill in the art are considered as being within the metes and bounds of the instant disclosure.

Figure 6:
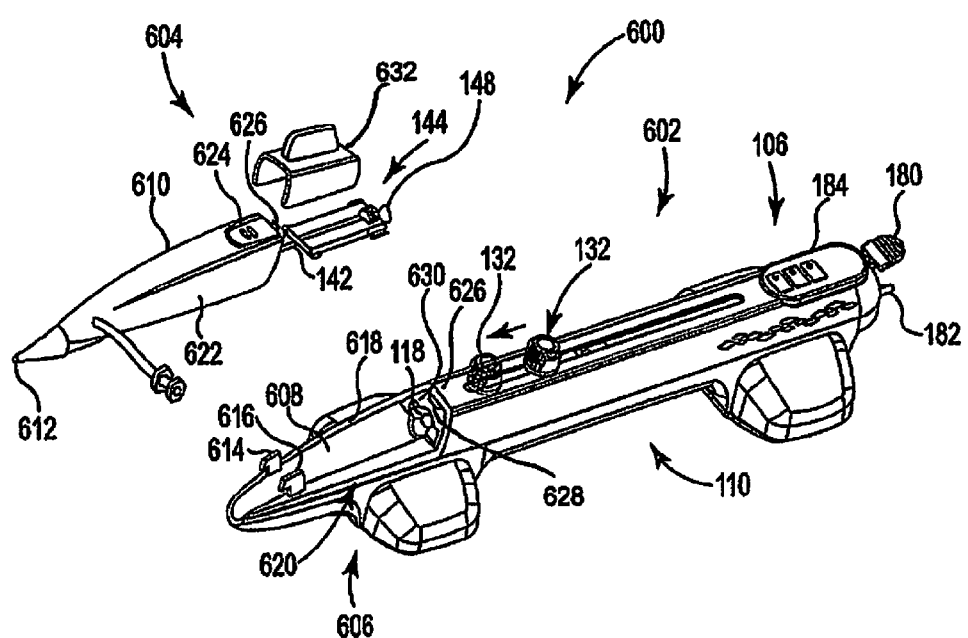
FIG. 6 is a perspective view of yet another embodiment of a rotational atherectomy device in a dis-assembled state.

FIG. 6 is a perspective view of yet another embodiment of a rotational atherectomy device 600 in a dis-assembled state. Elements and components of the device 600 that are substantially similar or the same as those in other embodiments of the device are identified with the same reference numerals. Device 600 includes a handle 602 and an exchangeable drive shaft cartridge 604, wherein the handle 602 and the drive shaft cartridge 604 include one or more connectors configured for removably connecting the handle 602 and the drive shaft cartridge 604 to one another. The handle 602 includes a proximal section 106, a distal section 606, and an elongated hollow intermediate section 110 extending between the proximal and distal sections 106 and 606, respectively. The intermediate section 110 includes the opening 118 between the interior 120 thereof and a trough 608 in the distal section 606 configured for receiving the gear engagement assembly 144. The drive shaft cartridge 604 includes a distal section 610 having an opening in a distal end 612 thereof configured for passage therethrough of the drive shaft 142 extending distally from the gear engagement assembly 144.

The handle 602 and the drive shaft cartridge 604 are removably connected by first inserting the gear engagement assembly 144 through the opening 118 into the interior 120 of the intermediate section 110. The gear engagement assembly 144 and the prime mover carriage 124 within the interior 120 are removably coupled as described elsewhere with reference to device 100. Then the handle 602 and the drive shaft cartridge 604 are removably connected by juxtaposing the distal sections 606 and 610, and displacing the handle 602 and the drive shaft cartridge 604 towards one another.

In FIG. 6, the device 600 is illustrated having a first and a second connector, each having complementary first and section sections configured for removably connecting the handle 602 and the drive shaft cartridge 604. The first section of the first connector is shown as opposing hooks 614 and 616 integrally formed with respective opposing side walls and/or edges 618 and 620 of the distal section 606. The complementary second section of the first connector includes hook receptors (not shown) for the hooks 614 and 616 are integrally formed with the opposing side walls and/or edges, e.g., wall/edge 622, of the distal section 610. The hook receptors are configured for removably receiving the hooks 614 and 616. When the juxtaposed handle 602 and the drive shaft cartridge 604 are displaced towards one another, the hooks 614 and 616 are slidably and removably received in the hook receptors in the distal section 610.

The second connector for removably connecting the handle 602 and the drive shaft cartridge is a tabbed connector. The first section of the tabbed connector is shown as a tab 624 integrally formed with the distal section 610 at a proximal end (or edge or wall) 626 thereof. The complementary second section of the second connector is shown as a tab receptor 628 integrally formed with the handle 602 at a distal end (or edge or wall) 630 of the intermediate section 110. The tab receptor 628 is configured for slidably and removably receiving at least a portion of the tab 624. When the juxtaposed handle 602 and the drive shaft cartridge 604 are displaced towards one another, the tab 624 is slidably and removably received by the tab receptor on the handle 602.

In some embodiments, the device 600 includes one or more alignment elements having complementary first and second sections configured for aligning the distal sections 606 and 610 with one another in preparation for or while removably connecting the handle 602 and the drive shaft cartridge 604 with one another. In certain embodiments, the one or more alignment elements are configured as tongueand-groove elements integrally formed with side edges of the distal sections 606 and 610.

In some embodiments, the first and the second connectors operate concurrently for removably connecting the handle 602 and the drive shaft cartridge 604. In certain embodiments, one of the first and the second connectors operates before the other. Additionally or in the alternative, one or both of the first and the second connectors may be configured as a first and a second alignment element for aligning the distal sections 606 and 610, respectively, of the handle 602 and the drive shaft cartridge 604.

For replacing or exchanging an installed drive shaft cartridge 604 with another, the first and the second connector are operated to disengage their respective first and second sections, and the handle 602 and the drive shaft cartridge 604 are displaced away from one another The gear engagement assembly 144 is then removed from the intermediate section 110 through the opening 118. Some embodiments of the device 600 include a support 632 for holding the gear engagement assembly 144 proximate the opening 118 and aligning them prior to inserting the gear engagement assembly 144 into the interior 120 of the intermediate section 110 through the opening 118. The support 632 can also be used for holding the gear engagement assembly 144 when it is removed from the interior 120 of the intermediate section 110 through the opening 118. The support 632 may also be configured for protecting at least a portion of the gear engagement assembly 144, including the drive shaft gear 148, while the handle 602 and the drive shaft cartridge 604 are not connected.

While specific configurations have been described with reference to the first and the second connector and with reference to the one or more alignment elements, additional and/or alternative embodiments will become apparent to those having ordinary skill in the art. All such additional and/or alternative embodiments configured for providing the same or substantially similar functionalities are considered as being within the metes and bounds of the instant disclosure.

Figure 7A:
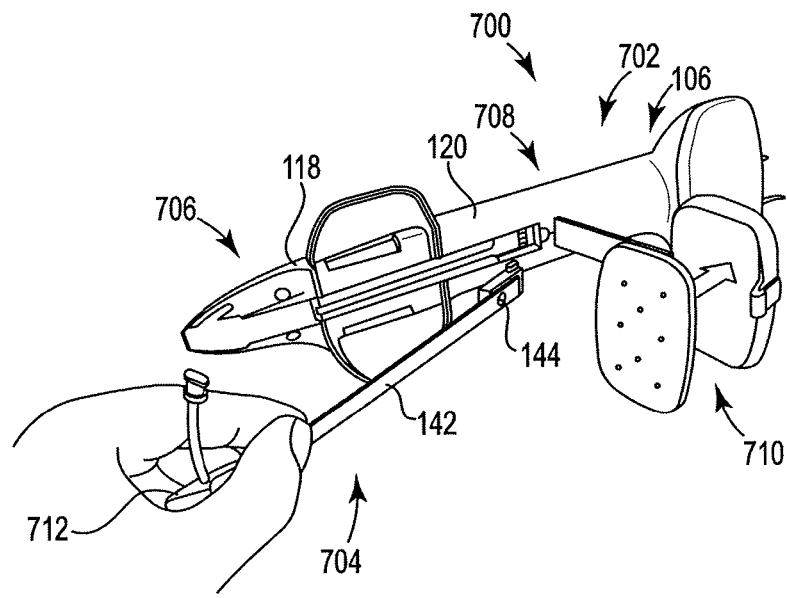
FIG. 7A is a perspective view of an embodiment of a rotational atherectomy device.

FIG. 7A is a perspective view of an embodiment of a rotational atherectomy device 700 in a dis-assembled state. Elements and components of the device 700 that are substantially similar or the same as those in other embodiments of the device are identified with the same reference numerals. Device 700 includes a handle 702 and an exchangeable drive shaft cartridge 704, wherein the handle 702 and the drive shaft cartridge 704 include one or more connectors configured for removably connecting the handle 702 and the drive shaft cartridge 704 to one another. The handle 702 includes the proximal section 106, a distal section 706, and an elongated hollow intermediate section 708 extending between the proximal and distal sections 106 and 706, respectively. The intermediate section 708 includes a door 710 operable for accessing the interior 120 thereof, and the opening 118 between the interior 120 and the trough or channel 112 in the distal section 706. The drive shaft cartridge 704 includes the drive shaft 142 extending distally from the gear engagement assembly 144, and a distal section 712 having an opening at a distal end thereof through which the drive shaft 142 extends. Although not shown, and as with other embodiments of the device, the device 700 includes one or more connectors each having complementary first and second section configured for removably connecting the distal sections 706 and 712 to one another. As with other embodiments of the device, the device 700 can include one or more alignment elements.

Figure 7B:
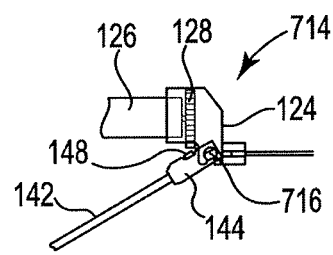
FIG. 7B is a side view illustrating an embodiment of a pivoting connector for a prime mover carriage and an exchangeable drive shaft cartridge in the device of FIG. 7A.

FIG. 7B is a detailed side view illustrating a pivoting connector 714 configured for removably and pivotably coupling the prime mover carriage 124 and the gear engagement assembly 144 to one another. The pivoting connector 714 is further configured for aligning and meshing the prime mover gear 128 and the drive shaft gear 148. The pivoting connector 714 includes a pivot point or axis 716 and complementary first and second sections integrally formed with the prime mover carriage 124 and the gear engagement assembly 144. The prime mover carriage 124 and the gear engagement assembly 144 are pivotably and removably connected at their respective first and second sections.

For "loading" the device 700, the interior 120 of the intermediate section 708 is exposed by opening the door 710. The prime mover carriage 124 and the gear engagement assembly 144 are pivotably and removably coupled at the pivot point or axis 716 of the pivoting connector 714 such that the prime mover gear 138 and the drive shaft gear 148 are aligned. Next, the distal sections 706 and 712 are juxtaposed by displacing them towards each other by rotating the handle 702 and the drive shaft cartridge 704 about the pivot point or axis 716. The prime mover gear 138 and the drive shaft gear 148 will be meshed when the distal sections 706 and 712 are removably connected. Thereafter, the door 710 is closed, and the device 700 is ready for use. For "unloading" the device 700, the process for "loading" the device 700 is performed in reverse.

Figure 8:
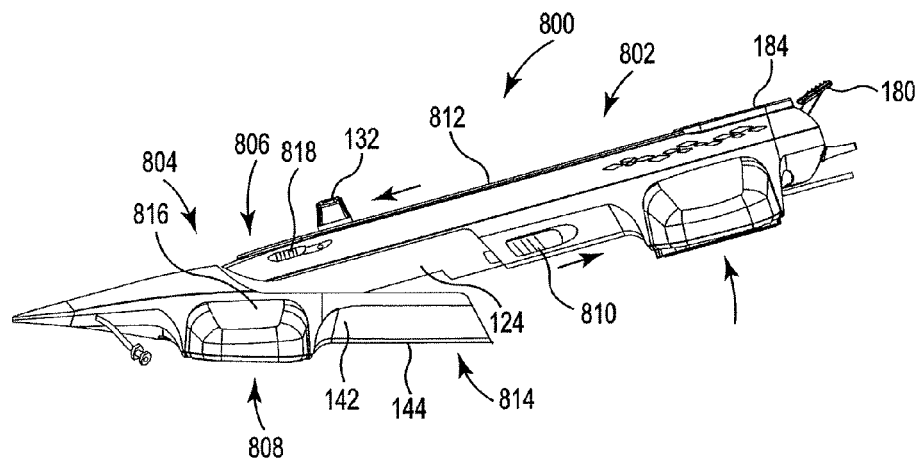
FIG. 8 is a side view of another embodiment of a rotational atherectomy device.

FIG. 8 is a side view of another embodiment of a rotational atherectomy device 800 in a partially dis-assembled state. Elements and components of the device 800 that are substantially similar or the same as those in other embodiments of the device are identified with the same reference numerals. Device 800 includes a handle 802 and an exchangeable drive shaft cartridge 804 configured for being removably connected. In some embodiments, the device 800 includes a first connector and a second connector, each having complementary first and second sections configured for removably connecting the handle 802 and the drive shaft cartridge 804 to each other.

In FIG. 8, the first connector is illustrated as a pivoting connector having a first section integrally formed with a distal section 806 of the handle 802, and a second section integrally formed with an intermediate section 808 of the drive shaft cartridge 804. The second connector is illustrated as a tabbed connector wherein the first section is a slidable tab 810 integrally formed with an elongated hollow intermediate section 812 of the handle 802, and wherein the second section is a tab receptor (not shown) integrally formed with a proximal section 814 of the drive shaft cartridge 804. The illustrated locations of the first and the second connectors are primarily for the purpose of describing the device 800. Of course, the complementary first and second sections, respectively, of the first and the second connector can be formed elsewhere on the handle 802 and the drive shaft cartridge 804 subject to providing the required functionality, including ensuring that the prime mover gear 128 and the drive shaft gear 148 will be aligned for proper meshing when the handle 802 and the drive shaft cartridge 804 are removably connected.

For "loading" the device 800, the first and second sections of the first connector are used for pivotably and removably connecting the distal section 806 of the handle 802 and the intermediate section 808 of the drive shaft cartridge 804 with one another. Next, the intermediate section 812 of the handle 802 and the proximal section 814 of the drive shaft cartridge 804 are juxtaposed by displacing them towards each other by rotating the handle 802 and the drive shaft cartridge 804 about a pivot point or axis 816 of the pivotable first connector. Then, the prime mover carriage 124 and the gear engagement assembly 144 are positioned such that the prime mover gear 128 and the drive shaft gear 148 are aligned. Thereafter, the first and second sections of the second connector will operate, automatically or manually, to removably connect the intermediate section 812 and the proximal section 814 to one another. And, the prime mover gear 128 and the drive shaft gear 148 will be meshed. The second connector can also be operated to dis-connect the intermediate section 812 of the handle 802 and the proximal section 814 of the drive shaft cartridge 804 from one another.

Some embodiments of the device 800 include a third connector having complementary first and second sections for removably connecting the handle 802 and the drive shaft cartridge 804 to one another at locations in addition to or alternatively to the first and the second connectors. FIG. 8 illustrates a third connector for an additional removable connection between the handle 802 and the drive shaft cartridge 804. In some embodiments, the third connector is configured as a tabbed connector having a first section 818 integrally formed with the intermediate section 812 of the handle 802, and the second section integrally formed with the intermediate section 808 of the drive shaft cartridge 804. The third connector can be configured for operating automatically or by a user of the device 800 after or concurrently with the second connector.

For "unloading" the device 800, the process for "loading" the device 800 is performed in reverse. As with other embodiments of the device, the device 800 can include one or more alignment elements.

Figure 9:
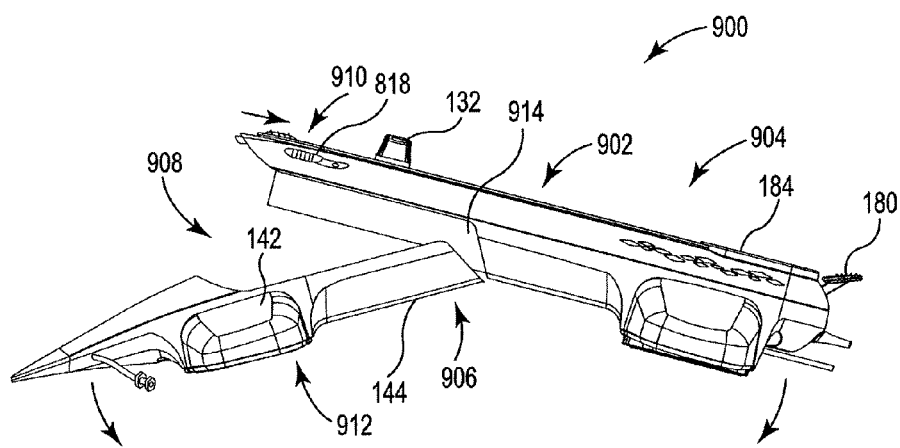
FIG. 9 is a side view of yet another embodiment of a rotational atherectomy device.

FIG. 9 is a side view of yet another embodiment of a rotational atherectomy device 900 in a partially dis-assembled state Elements and components of the device 900 that are substantially similar or the same as those in other embodiments of the device are identified with the same reference numerals. With reference to FIGS. 8 and 9, it should be apparent that the respective illustrated devices 800 and 900 are substantially similar to each other. One difference between the devices 800 and 900 is that locations of the first and the second connectors are swapped. Specifically, the first connector, configured as a pivoting connector, pivotably and removably connects an elongated hollow intermediate section 902 of a handle 904 to a proximal section 906 of an exchangeable drive shaft cartridge 908. And, the second connector, configured as a tabbed connector, removably connects a distal section 910 of the handle 904 and an intermediate section 912 of the drive shaft cartridge 908 to one another.

For "loading" the device 900, the first and second sections of the first connector are used for pivotably and removably connecting the intermediate section 902 of the handle 904 and the proximal section 906 of the drive shaft cartridge 908 to one another. Next, the prime mover carriage 124 and the gear engagement assembly 144 are position such that the prime mover gear 128 and the drive shaft gear 148 are aligned. Then, the distal section 910 of the handle 904 and the intermediate section 912 of the drive shaft cartridge 908 are juxtaposed by displacing them towards each other by rotating the handle 904 and the drive shaft cartridge 908 about a pivot point or axis 914 of the pivotable first connector. Thereafter, the first and second sections of the second connector will operate, automatically or manually, to removably connect the distal section 910 of the handle 904 and the intermediate section 912 of the drive shaft cartridge 904 to one another. And, the prime mover gear 128 and the drive shaft gear 148 will be meshed. The second connector can also be operated to dis-connect the distal section 910 of the handle 904 and the intermediate section 912 of the drive shaft cartridge 904 from one another. As with device 800, the device 900 can also include a substantially similar third connector.

For "unloading" the device 900, the process for "loading" the device 900 is performed in reverse. As with other embodiments of the device, the device 900 can include one or more alignment elements.

Figure 10:
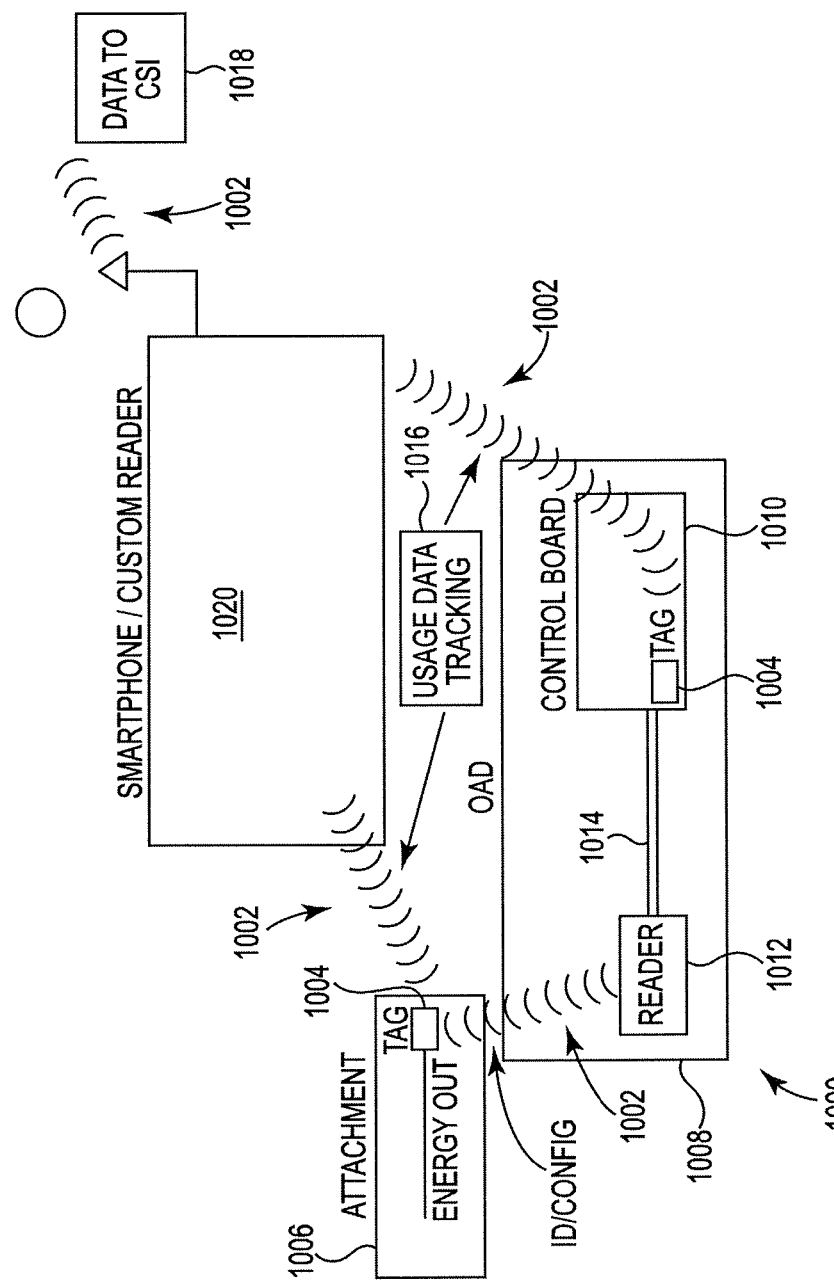
FIG. 10 is a block diagram representation of an embodiment of a system for performing an atherectomy procedure.

FIG. 10 illustrates an embodiment of a system 1000 configured for identifying, monitoring, and controlling the operation of a plurality of devices and components used for performing atherectomy. In some embodiments, at least a portion of the system 1000 is configured for wireless or contact-less communications 1002 between two or more devices and components used for performing atherectomy. In certain non-limiting exemplary embodiments, the mode of communications 1002 includes one or more of radio frequency (RF) and infra-red (IR), among others. In some embodiments, the system 1000 includes one or more wireless or contact-less identification tags, e.g., NFC/RFID tag, 1004 disposed on one or more devices and components of a rotational or orbital atherectomy device. In a non-limiting exemplary embodiments, the one or more identification tags 1004 provide a contact-less means for identifying different shafts/crowns or accessories 1006 attached to a rotational or orbital atherectomy device (OAD) 1008. The identifying information would allow the main control board 1010 to vary its operational parameters as needed to properly control or interface with the attachment 1006. In certain embodiments, the one or more identification tags can be disposed on one or more devices and/or components used with the OAD.

In a non-limiting exemplary embodiment, the one or more identification tags 1004 can be disposed on a removable portion of the OAD and, when attached to the main body of the device, an NFC/RFID reader 1012 would identify the attachment 1006 and obtain its operational parameters. The reader 1012 then communicates 1014 this information to the control board 1010. In some embodiments, the one or more identification tags 1004 are configured for storing data that can be used for analysis. In certain embodiments, device and/or component usage statistics such as, total run time, time spent at various speeds, etc., can be used for generating a snapshot of the atherectomy procedure.

In some embodiments, the one or more identification tags 1004 can be used as a safety mechanism such as not allowing the OAD to operate if a required attachment is not connected. In certain embodiments, the one or more identification tags can be used for inventory management and tracking data 1016 that can be collected in the field and transmitted to a remote center, e.g., remote servers, 1018. In a non-limiting exemplary embodiment, WiFi and/or cellular networks can be used for the transmission using a smartphone 1020 after collecting the data from the tag 1004.

In certain embodiments, the one or more identification tags are configured for harvesting energy for providing energy or power for operating the one or more components and devices of the system 1000. Some non-limiting exemplary embodiments for harvesting energy include harvesting RF energy.

The descriptions of the embodiments and their applications as set forth herein should be construed as illustrative, and are not intended to limit the scope of the disclosure. Features of various embodiments may be combined with other embodiments and/or features thereof within the metes and bounds of the disclosure. Upon study of this disclosure, variations and modifications of the embodiments disclosed herein are possible, and practical alternatives to and equivalents of the various elements of the embodiments will be understood by and become apparent to those of ordinary skill in the art. Such variations and modifications of the embodiments disclosed herein may be made without departing from the scope and spirit of the invention. Therefore, all alternatives, variations, modifications, etc., as may become to one of ordinary skill in the art are considered as being within the metes and bounds of the instant disclosure.

What is claimed is:

1. A device, comprising:
   a handle, comprising:
      a proximal section;
      a distal section comprising a trough; and
      an elongated hollow intermediate section between the proximal and the distal sections, the intermediate section comprising:
         an opening between an interior thereof and the trough; and
         a slot;
   a prime mover carriage comprising a prime mover, the prime mover carriage disposed within the interior of the intermediate section;
   a prime mover gear fixedly attached to a shaft of the prime mover;
   a control knob having at least a portion thereof extending through the slot and operationally coupled to the prime mover carriage such that a longitudinal displacement of the control knob induces a longitudinal displacement of the prime mover carriage, the control knob comprising:
      an unlocked state for permitting the longitudinal displacement of the control knob; and
      a locked state for inhibiting the longitudinal displacement of the control knob;
   an exchangeable drive shaft cartridge, comprising:
      a proximal section and a distal section;
      a drive shaft comprising a proximal end and a distal end, the drive shaft extending through an opening in a distal end of the drive shaft cartridge; and
      a gear engagement assembly comprising a drive shaft gear fixedly attached to the proximal end of the drive shaft; and
   one or more connectors for removably connecting the handle and the drive shaft cartridge to one another, wherein each of the one or more connectors comprises complementary first and second sections, wherein
      the first section is integrally formed with the handle; and
      the second section is integrally formed with the drive shaft cartridge;
   wherein, the handle and the drive shaft cartridge are removably connected by:
      inserting at least the gear engagement assembly through the opening in the intermediate section of the handle;
      removably meshing the prime mover gear and the drive shaft gear by juxtaposing the prime mover carriage and the gear engagement assembly; and
   displacing the handle and the drive shaft cartridge in opposite directions;
      at least one alignment element for aligning at least the prime mover gear and the drive shaft gear with one another, the at least one alignment element comprising complementary first and second sections, wherein the first section of the at least one alignment element is integrally formed with the prime mover carriage; and the second section of the at least one alignment element is integrally formed with the gear engagement assembly;
   at least one biasing element configured for removably meshing the prime mover gear and the drive shaft gear when the prime mover gear and the drive shaft gear are aligned with one another such that a rotational movement of one of the prime mover and the drive shaft induces a rotational movement in the other, wherein the at least one biasing element comprises a ramp configured for pivoting at least one of the prime mover gear and the drive shaft gear towards the other.

2. The device of claim 1, wherein the at least one alignment element is configured for aligning at least the prime mover gear and the drive shaft gear with one another when the gear engagement assembly is extended into the interior of the intermediate section and positioned proximate the prime mover.

3. The device of claim 1, wherein the one or more connectors are selected from the group consisting of snap-fit connectors, tongue and groove connectors, rails, bayonet mount, and ribs.

4. The device of claim 1, wherein the opening in the intermediate section of the handle is configured for passage therethrough of the gear engagement assembly and at least a portion of the drive shaft extending distally from the drive shaft gear.

5. The device of claim 1, wherein the proximal section of the handle comprises one of a guide wire clamp and a guide wire brake mechanism.

6. The device of claim 1, wherein the interior of the intermediate section of the handle is configured for:
   longitudinal displacement of the prime mover carriage disposed therewithin;
   longitudinal displacement of the gear engagement assembly inserted therein; and
   longitudinal displacement of the drive shaft.

7. The device of claim 1, wherein the longitudinal displacement of the prime mover carriage induces a longitudinal displacement of the gear engagement assembly and of the drive shaft extending from the gear engagement assembly when the distal section of the handle and the distal section of the drive shaft cartridge are removably connected.

8. The device of claim 1, wherein at least a portion of the drive shaft is telescoping.

9. The device of claim 1, wherein the prime mover is selected from the group consisting of a turbine and an electric motor.

10. The device of claim 1, comprising one or more sensors for monitoring a rotational speed of at least one of the prime mover shaft and the drive shaft.

11. The device of claim 1, comprising:
   a lumen having the drive shaft disposed therewithin;
   a fluid infusion port in fluid communication with the lumen; and
   a fluid reservoir in fluid communication with the fluid infusion port;
   wherein, the fluid infusion port is configured for delivering fluid from the fluid reservoir to the lumen.

12. The device of claim 1, wherein the distal end of the drive shaft is configured for insertion into a vasculature.

13. The device of claim 12, comprising an abrasive element proximate the distal end of the drive shaft.

14. The device of claim 1, wherein the prime mover carriage is positioned distally within the intermediate section of the handle before inserting the gear engagement assembly through the opening in the intermediate section of the handle.

15. The device of claim 1, comprising at least one disconnect mechanism for disconnecting the removably connected handle and the drive shaft cartridge.

\* \* \* \* \*